United States Patent
Kain

(10) Patent No.: US 11,449,492 B2
(45) Date of Patent: Sep. 20, 2022

(54) COMMUNITY DATA AGGREGATION WITH COHORT DETERMINATION

(71) Applicant: LunaPBC, Solana Beach, CA (US)

(72) Inventor: Robert C. Kain, San Diego, CA (US)

(73) Assignee: LunaPBC, Solana Beach, CA (US)

(*) Notice: Subject to any disclaimer, the term of this patent is extended or adjusted under 35 U.S.C. 154(b) by 447 days.

(21) Appl. No.: 16/399,355

(22) Filed: Apr. 30, 2019

(65) Prior Publication Data

US 2020/0210405 A1    Jul. 2, 2020

Related U.S. Application Data

(63) Continuation of application No. PCT/US2018/067933, filed on Dec. 28, 2018.

(51) Int. Cl.
*G06F 16/00* (2019.01)
*G06F 16/23* (2019.01)
(Continued)

(52) U.S. Cl.
CPC ........ *G06F 16/2365* (2019.01); *G06F 16/215* (2019.01); *G06F 16/244* (2019.01);
(Continued)

(58) Field of Classification Search
CPC ........... G06F 16/2365; G06F 16/24556; G06F 16/215; G06F 11/14; G06F 16/244;
(Continued)

(56) References Cited

U.S. PATENT DOCUMENTS 5,974,409 A    10/1999 Sanu et al.
6,208,991 B1    3/2001 French et al.
(Continued)

FOREIGN PATENT DOCUMENTS

WO    2014/042942 A1    3/2014
WO    2015/123540 A1    8/2015
(Continued)

OTHER PUBLICATIONS

Bovenberg, Jasper A; "One Sample, One Share! A Proposal to Redress an Inequity with Equity;" Biobanks and Tissue Research. The Public, the Patient and the Regulation; Jan. 2011; 16 pages.
(Continued)

*Primary Examiner* — Noosha Arjomandi
(74) *Attorney, Agent, or Firm* — Fletcher Yoder P.C.

(57) ABSTRACT

A system and method are disclosed for the collection and aggregation of data from contributing members of a community, such as health-related, personal, genomic, medical, and other data of interest for individuals and populations. Contributors become members of a community upon creation of an account and providing of data or files. The data is received and processed, such as to analyze, structure, perform quality control, and curate the data. Value or shares in one or more community databases are computed and attributed to each contributing member. The data is controlled to avoid identification or personalization. Steps are taken to determine incompleteness and incorrectness of the data, and the data may be improved or completed automatically, based upon interaction with members, additional contributions of data, and so forth.

32 Claims, 12 Drawing Sheets

(51) Int. Cl.
  *G06F 16/2455* (2019.01)
  *G06F 16/215* (2019.01)
  *G06F 16/242* (2019.01)
  *H04L 9/06* (2006.01)
  *H04L 9/00* (2022.01)
(52) U.S. Cl.
  CPC ...... *G06F 16/24556* (2019.01); *H04L 9/0637* (2013.01); *H04L 9/0643* (2013.01); *H04L 9/50* (2022.05); *H04L 2209/56* (2013.01)
(58) Field of Classification Search
  CPC ....... H04L 9/0637; H04L 9/0643; H04L 9/50; H04L 2209/56; G16H 10/60; G16H 80/00; G16H 40/20
  See application file for complete search history.

(56) References Cited

U.S. PATENT DOCUMENTS

| | | | |
|---|---|---|---|
| 7,181,375 | B2 | 2/2007 | Rao et al. |
| 7,306,562 | B1 | 12/2007 | Baykal |
| 8,589,437 | B1* | 11/2013 | Khomenko ............ G16B 50/30 |
| | | | 707/941 |
| 8,589,589 | B2 | 11/2013 | Clemm et al. |
| 9,110,553 | B2 | 8/2015 | Ash et al. |
| 9,489,656 | B2 | 11/2016 | Yoo et al. |
| 9,536,052 | B2 | 1/2017 | Amarasingham et al. |
| 10,025,877 | B2 | 7/2018 | Macpherson |
| 10,162,880 | B1 | 12/2018 | Chowdry et al. |
| 10,172,517 | B2 | 1/2019 | Jain et al. |
| 10,594,757 | B1* | 3/2020 | Shevchenko ........... G06F 40/35 |
| 10,621,164 | B1* | 4/2020 | Kain ..................... G06F 16/215 |
| 11,321,522 | B1* | 5/2022 | Shevchenko ......... G06F 40/186 |
| 2002/0095585 | A1 | 7/2002 | Scott |
| 2003/0040002 | A1 | 2/2003 | Ley |
| 2004/0034550 | A1 | 2/2004 | Menschik et al. |
| 2005/0010435 | A1 | 1/2005 | Kato et al. |
| 2005/0108551 | A1 | 5/2005 | Toomey |
| 2005/0119534 | A1 | 6/2005 | Trost et al. |
| 2005/0132104 | A1 | 6/2005 | Brown |
| 2006/0129427 | A1 | 6/2006 | Wennberg |
| 2006/0173663 | A1 | 8/2006 | Langheier et al. |
| 2007/0055552 | A1 | 3/2007 | St. Clair et al. |
| 2007/0136378 | A1 | 6/2007 | Karpf et al. |
| 2007/0258902 | A1 | 11/2007 | Hwang et al. |
| 2007/0276768 | A1 | 11/2007 | Pallante |
| 2008/0081331 | A1 | 4/2008 | Myres et al. |
| 2008/0120296 | A1 | 5/2008 | Kariathungal et al. |
| 2008/0131887 | A1 | 6/2008 | Stephan et al. |
| 2008/0177799 | A1 | 7/2008 | Wilson |
| 2008/0222299 | A1 | 9/2008 | Boodaei |
| 2008/0313262 | A1 | 12/2008 | Cho et al. |
| 2009/0055217 | A1 | 2/2009 | Grichnik et al. |
| 2009/0132282 | A1 | 5/2009 | Kerstna et al. |
| 2010/0047803 | A1 | 2/2010 | Weinshilboum et al. |
| 2010/0145953 | A1 | 6/2010 | Charles et al. |
| 2010/0249531 | A1* | 9/2010 | Hanlon .................. G16H 50/50 |
| | | | 600/300 |
| 2010/0316251 | A1 | 12/2010 | Cowburn et al. |
| 2010/0331146 | A1 | 12/2010 | Kil |
| 2011/0129131 | A1* | 6/2011 | Avinash ................. G16H 50/20 |
| | | | 382/128 |
| 2013/0185421 | A1 | 7/2013 | Orr et al. |
| 2013/0246097 | A1* | 9/2013 | Kenney .................. G16H 10/60 |
| | | | 705/3 |
| 2014/0012843 | A1 | 1/2014 | Soon-Shiong |
| 2014/0046680 | A1 | 2/2014 | Wentz et al. |
| 2014/0095201 | A1 | 4/2014 | Farooq et al. |
| 2014/0164003 | A1 | 6/2014 | Thesman |
| 2014/0222966 | A1 | 8/2014 | Marins et al. |
| 2014/0229495 | A1 | 8/2014 | Makkapati et al. |
| 2014/0324466 | A1 | 10/2014 | Wertzberger |
| 2015/0074760 | A1 | 3/2015 | Yan et al. |
| 2015/0235006 | A1 | 8/2015 | Nichols |
| 2015/0244690 | A1 | 8/2015 | Mossbarger |
| 2015/0294069 | A1 | 10/2015 | Shah |
| 2015/0332283 | A1 | 11/2015 | Witchey |
| 2015/0379510 | A1 | 12/2015 | Smith |
| 2016/0055236 | A1 | 2/2016 | Frank et al. |
| 2016/0210692 | A1 | 6/2016 | Perez |
| 2017/0140477 | A1 | 5/2017 | Heywood et al. |
| 2017/0329904 | A1* | 11/2017 | Naughton .............. G16B 50/10 |
| 2018/0039737 | A1 | 2/2018 | Dempers et al. |
| 2018/0294047 | A1 | 10/2018 | Hosseini et al. |
| 2018/0294048 | A1 | 10/2018 | Blumenthal et al. |
| 2018/0307859 | A1 | 10/2018 | LaFever et al. |
| 2018/0330824 | A1 | 11/2018 | Athey et al. |
| 2018/0341648 | A1* | 11/2018 | Kakavand ............. G06F 21/645 |
| 2018/0368819 | A1 | 12/2018 | Gogineni |
| 2019/0006048 | A1 | 1/2019 | Gupta et al. |
| 2019/0020651 | A1 | 1/2019 | Soon-Shiong et al. |
| 2019/0026425 | A1 | 1/2019 | Downs et al. |
| 2019/0156923 | A1* | 5/2019 | Kain ....................... G16H 10/20 |
| 2019/0304578 | A1* | 10/2019 | Kain ....................... G16H 10/20 |
| 2020/0203012 | A1* | 6/2020 | Kamath ................ A61B 5/1455 |
| 2020/0210392 | A1* | 7/2020 | Kain ..................... G06F 16/244 |

FOREIGN PATENT DOCUMENTS

| | | |
|---|---|---|
| WO | 2015/157572 A1 | 10/2015 |
| WO | 2015/171580 A1 | 11/2015 |
| WO | 2016/005793 A1 | 1/2016 |
| WO | 2016/077727 A1 | 5/2016 |
| WO | 2016/189488 A2 | 12/2016 |
| WO | 2017/136643 A1 | 8/2017 |
| WO | 2017/146363 A1 | 8/2017 |
| WO | 2017/209446 A1 | 12/2017 |
| WO | 2018/177663 A1 | 10/2018 |
| WO | 2018/177664 A1 | 10/2018 |

OTHER PUBLICATIONS

International Search Report and Written Opinion for PCT/US2018/067933 dated Sep. 18, 2019; 15 pages.

International Search Report and Written Opinion for PCT/US2018/061419 dated Feb. 25, 2019, 14 pages.

* cited by examiner

COMMUNITY DATA AGGREGATION WITH COHORT DETERMINATION

CROSS-REFERENCE TO RELATED APPLICATIONS

This application is a continuation of and claims priority to PCT Application No. PCT/US2018/067933, entitled "COMMUNITY DATA AGGREGATION, COMPLETION, CORRECTION AND USE", filed on Dec. 28, 2018, which is hereby incorporated by reference in its entirety.

BACKGROUND

The present invention relates to techniques for filling important gaps in data, particularly in health-related data, including electronic health record (EHR) data and patient reported outcomes (PRO) data, but also in a wide range of data types, such as omic data, personal data, demographic data, and so forth. The invention also relates to platforms and approaches to aggregating data from contributing members of a community, compensating or motivating contributing members, and utilizing the data to aid both members and a larger community.

The value of big data has become generally accepted, creating an industry drive to aggregate different types of data in order to use machine learning and other tools to drive discovery. At scale even weak data can be valuable in unlocking links between our health and our genomic information and our daily habits, such as diet, exercise, drinking, smoking, hours of sleep, etc. Therefore, it is valuable to collect an individual's data from health institutions and through direct surveys and interviews. Additionally, it is now possible to collect implicit data through grocery store loyal customer tracking of purchase records, credit card records, online search habits, etc.

In all cases, even though at an aggregate level the data is valuable, there is a significant amount of missing information. Some examples are EHR and PRO data. EHRs are typically filled out by doctors online while meeting with patients. There are at least two types of challenges with these records. First, EHRs are designed primarily as billing systems for medical institutions. They record patient information such as test results, symptoms, and doctors' observations and recommendations, including treatment prescriptions. They do not typically record outcomes after treatment or whether patients followed the prescribed treatment regime. Moreover, doctors and other health professionals do not always use digital entry fields to record information. They often simply write information in unstructured comment fields. Additionally, the nomenclature and ontology used when inputting data is not standardized. There is a major challenge associated with deciphering and decrypting these free form comments.

In the case of PRO records, often patient outcomes are never reported in a system. There is no current method for identifying even when a PRO should be sought. Additionally, PROs might be required periodically over a long period of time. Some diseases and corresponding treatments may last months, years, or be persistent over a lifetime. The longitudinal information that would come from PROs is valuable in determining efficacy of treatments and in stratifying diseases diagnosed based on symptoms, to determine the underlying molecular basis for the disease.

To data solutions to fill in the holes and acquire the missing information have all been focused on using humans to review the data, identify mission information, and manually attempt to fill the gaps. People can for instance read EHR records, including fee form fields, and then populate the digital fields accordingly. Additionally surveyors call individuals and through in person interview they identify PROs, and input the corresponding information into digital database fields. In all cases the solution requires the intervention of an individual, and it is therefor not scalable in terms of labor hours or labor dollars for use with databases of tens of thousands to millions of individuals.

Beyond EHR and PRO data, many other data types may be extremely useful in piecing together an overall picture of the condition, state, or health of an individual and of groups of individuals, as well as for assessing possible pathways for maintaining health, avoiding or treating disease, recognizing and developing treatments, and so forth. But such pathways are hindered by missing or inaccurate data, and by typical "siloing" of data by separate sources, institutions, and so forth, often with no ill intent, and many times with patient or individual confidentiality in mind. At the same time, social media platforms may almost certainly share data, but again typically silo the data for their own purposes, and quite often even without any control by the individuals involved, and little or no quality control.

There is a need for improved technologies for data gathering and quality control, which scalable data aggregation and use. There is a particular need for such technologies that may enhance the control and motivate participation by contributing individuals, while protecting their privacy.

BRIEF DESCRIPTION

In accordance with one aspect of the disclosure, a system comprises a server that, in operation, facilitates interaction with contributing members of an aggregation; a centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data. The processing circuitry analyzes the member-specific contributed data for each member to determine missing or incorrect data, and sends a de-identified communication to respective member to provide missing data or to correct incorrect data.

In accordance with some embodiments, the processing circuitry may determine a quality score based upon the completeness and/or correctness of the member-specific contributed data; and/or the quality score is based at least partially on determined contradictions and/or inconsistencies in the member-specific contributed data; and/or the member-specific value is at least partially upon the quality score; and/or the processing circuitry automatically and without human intervention attempts to complete missing data and/or to correct incorrect data prior to communicating with the contributing member; and/or the database is configured to store member-specific contributed data of different types, and the processing circuitry determines missing or incorrect data of one type based upon analysis of data of a different type; and/or the types of member-specific contributed data comprise at least two of omic data, phenotype data, health data, personal data, familial data and environmental data; and/or the database is configured to store member-specific contributed data of different types, and the processing circuitry determines missing or incorrect data of one type based upon analysis of the same type of data but contributed at different times by the same contributing member; and/or the missing or incorrect data is determined based upon analysis of aggregated data of a plurality of contributing members; and/or the missing or incorrect data comprises at least two of personal data, medical record data, dietary data and wearable device data; and/or the communication comprises a customized survey based upon data determined to be missing and/or incorrect; and/or the communication comprises a recommendation for acquisition of additional data by the contributing member; and/or the processing circuitry transfers an asset amount to each member-specific account based upon the member-specific value; and/or the user-specific value is attributed as a currency and/or a cryptocurrency and/or an ownership share in the database; and/or the processing circuitry is configured to make ledger entries in an immutable and/or cryptographically encoded ledger and/or a blockchain based upon interaction with the contributing members.

In accordance with another aspect of the disclosure, a system comprises a server that, in operation, facilitates interaction with contributing members of an aggregation; a centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data, wherein the processing circuitry analyzes the member-specific contributed data for each member to determine missing or incorrect data; and wherein the database is configured to store member-specific contributed data of different types, and the processing circuitry automatically and without human intervention, provides and/or corrects missing or incorrect data of one type based upon analysis of data of a different type or from a separate contribution event, the types of member-specific contributed data comprise at least two of omic data, phenotype data, health data, personal data, familial data and environmental data.

In accordance with some embodiments of this technique, the database comprises an immutable and/or cryptographically encoded and/or tamper-evident ledger; the processing circuitry sends a de-identified communication to respective contributing members to provide or correct missing or incorrect data, or to confirm the automatic provision of the missing or incorrect data; or any of the specific variations mentioned above may be combined with these embodiments.

In accordance with a further aspect of the disclosure, a computer-implemented method comprises receiving, from the contributing members, member-specific account data and member-specific contributed data, the member-specific contributed data comprising health-related data submitted by each contributing member or data derived therefrom; storing, in a database, the member-specific contributed data; aggregating the member-specific contributed data with member-specific contributed data of other contributing members; establishing a member-specific account for each contributing member based on the member-specific account data; attributing a member-specific value to each member-specific account based upon member-specific contributed data of the respective contributing member; and processing the member-specific contributed data to determine missing or incorrect data, and sending a de-identified communication to respective member to provide missing data or to correct incorrect data.

In accordance with some embodiments of such methods, the database or another component of the system comprises an immutable and/or cryptographically encoded ledger and/or a blockchain. Any of the specific variations mentioned above may be combined with such methods.

In accordance with still another aspect of the disclosure, a system comprises a server that, in operation, facilitates interaction with contributing members of an aggregation; a centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data; wherein the processing circuitry analyzes the member-specific contributed data for each member to determine missing or incorrect data, and sends a de-identified communication to respective member to provide missing data or to correct incorrect data; and wherein the processing circuitry automatically and without human intervention attempts to complete missing data and/or to correct incorrect data prior to communicating with the contributing member.

In accordance with some embodiments of this system, the database is configured to store member-specific contributed data of different types, and the processing circuitry determines missing or incorrect data of one type based upon analysis of data of a different type or data contributed at a different time; and/or the processing circuitry attempts to complete missing data and/or to correct incorrect data of one type based upon analysis of a different type; and/or the processing circuitry attempts to complete missing data and/or to correct incorrect data of one contributing member based upon member-specific contributed data of at least one other contributing member; and/or the processing circuitry attempts to complete missing data and/or to correct incorrect data of one contributing member based upon aggregated member-specific contributed data of a plurality of other contributing members; and/or the types of member-specific contributed data comprise at least two of omic data, phenotype data, health data, personal data, familial data and environmental data; and/or the missing or incorrect data comprises at least two of personal data, medical record data, dietary data and wearable device data; and/or the communication comprises a customized survey based upon data determined to be missing and/or incorrect, or an invitation to provide additional data; and/or the processing circuitry determines a quality score based upon the completeness and/or correctness of the member-specific contributed data; and/or the quality score is based at least partially on determined contradictions and/or inconsistencies in the member-specific contributed data; and/or the processing circuitry re-evaluates the quality score after completion of incomplete data and/or correction of incorrect data; and/or the member-specific value is at least partially upon the quality score; and/or the processing circuitry re-evaluates the member-specific value after completion of incomplete data and/or correction of incorrect data; and/or the processing circuitry transfers an asset amount to each member-specific account based upon the member-specific value; and/or the user-specific value is attributed as a currency and/or a cryptocurrency and/or an ownership share in the database; and/or the processing circuitry is configured to make ledger entries in an immutable and/or cryptographically encoded ledger and/or a blockchain based upon interaction with the contributing members. Methods, including computer-implemented methods may be implemented to utilize such techniques, including any of the specific variations mentioned above.

In accordance with still another aspect of the disclosure, a system comprises a server that, in operation, facilitates interaction with contributing members of an aggregation; a centralized or virtually centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data; wherein the processing circuitry analyzes the member-specific contributed data for each member to determine missing or incorrect data, and sends a de-identified communication to respective member to provide missing data or to correct incorrect data; and wherein the processing circuitry automatically and without human intervention sends follow-up de-identified communications to specific contributing members to prompt contribution of follow-up member-specific contributed data based upon a physical condition of the respective contributing members.

In accordance with some embodiments of this aspect, the processing circuitry sends the follow-up de-identified communications periodically; and/or the processing circuitry sends the follow-up de-identified communications episodically; and/or the processing circuitry sends the follow-up de-identified communications based upon treatment regimes as indicated by the member-specific contributed data for the respective contributing members; and/or the processing circuitry sends the follow-up de-identified communications based upon a condition and/or disease diagnosis as indicated by the member-specific contributed data for the respective contributing members; and/or the follow-up de-identified communications comprise recommendations for acquisition of additional data of the respective contributing members; and/or the member-specific contributed data comprises health-related data, and the recommendations comprise at least one physical examination or test related to physical condition of the respective contributing members; and/or the processing circuitry analyzes the member-specific contributed data of each member to determine at least one most convenient and/or cost effective source for the acquisition of additional data, and the recommendations include an indication of the most convenient and/or cost effective source for each respective recommendation to each respective contributing member; and/or the follow-up communications for one contributing member are based upon member-specific contributed data of at least one other contributing member; and/or the follow-up communications for one contributing member based upon aggregated member-specific contributed data of a plurality of other contributing members; and/or types of member-specific contributed data comprise at least two of omic data, phenotype data, health data, personal data, familial data and environmental data; and/or the follow-up communications comprise a customized survey based upon the physical condition of the respective contributing members; and/or the processing circuitry re-evaluates the member-specific value after receipt of follow-up member-specific contributed data from each respective contributing member; and/or the follow-up communications comprise an indication to each contributing member of the re-evaluation of the member-specific value applicable when the respective contributing member contributes the follow-up member-specific contributed data; and/or the processing circuitry transfers an asset amount to each member-specific account based upon the member-specific value; and/or the user-specific value is attributed as a currency and/or a cryptocurrency and/or an ownership share in the database; and/or the processing circuitry is configured to make ledger entries in an immutable and/or cryptographically encoded ledger and/or a blockchain based upon interaction with the contributing members. Methods, including computer-implemented methods may be implemented to utilize such techniques, including any of the specific variations mentioned above.

In accordance with still another aspect of the disclosure, a system comprises a server that, in operation, facilitates interaction with contributing members of an aggregation; a centralized or virtually centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data; wherein the processing circuitry analyzes the aggregated member-specific contributed data to determine cohorts of contributing members based upon correlations between the member-specific contributed data for each contributing member.

In accordance with some embodiments of such systems, the processing circuitry determines the cohorts by periodic analysis of the aggregated member-specific contributed data; and/or the processing circuitry determines the cohorts by episodic analysis of the aggregated member-specific contributed data; and/or the processing circuitry determines the cohorts based upon analysis of the aggregated member-specific contributed data initiated by at least one contributing member; and/or the processing circuitry determines the cohorts based upon analysis of the aggregated member-specific contributed data initiated by identification of a physical condition potentially detectable from the aggregated member-specific contributed data; and/or the processing circuitry determines the cohorts based upon analysis of the aggregated member-specific contributed data initiated by identification of a new treatment of a physical condition detectable from the aggregated member-specific contributed data; and/or the processing circuitry determines the cohorts based upon analysis of the aggregated member-specific contributed data initiated by identification of a new examination, test, or omic pattern useful in determining a physical condition detectable from the aggregated member-specific contributed data; and/or the processing circuitry determines the cohorts without identification of the contributing members to the administrative entity; and/or the cohorts comprise contributing members sharing a physical condition; and/or the cohorts comprise contributing members sharing a disease state; and/or the cohorts comprise contributing members sharing a potential legal claim; and/or the processing circuitry permits communications between contributing members of a cohort without revealing identification of respective contributing members to the administrative entity; and/or the processing circuitry permits communications between contributing members of a cohort without revealing identification of respective contributing members to other contributing members unless such identification is done by the respective contributing members; and/or types of member-specific contributed data comprise at least two of omic data, phenotype data, health data, personal data, familial data, demographic data, employment data, and environmental data; and/or the determination of cohorts is initiated based upon analysis of one type of data followed by analysis of different types of data; and/or the processing circuitry permits contributing members to opt out of analysis to determine cohorts; and/or the processing circuitry permits contributing members to request that other members contribute additional data to enable or improve a statistical fit of data from potential cohort members of a determined cohort group; and/or the processing circuitry is configured to perform quality control operations on the contributed data prior to determination of the cohorts; and/or the processing circuitry transfers an asset amount to each member-specific account based upon the member-specific value; and/or the user-specific value is attributed as a currency and/or a cryptocurrency and/or an ownership share in the database; and/or the processing circuitry is configured to make ledger entries in an immutable and/or cryptographically encoded ledger and/or a blockchain based upon interaction with the contributing members. Methods, including computer-implemented methods may be implemented to utilize such techniques, including any of the specific variations mentioned above.

In accordance with yet another aspect of the disclosure, a system comprises a server that, in operation, facilitates interaction with contributing members of an aggregation; a centralized or virtually centralized database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data; and a template stored in database and including anticipated events or information in a patient health journey; wherein the processing circuitry automatically and without human intervention sends follow-up de-identified communications to specific contributing members to prompt contribution of follow-up member-specific contributed data based upon the template.

In accordance with some embodiments of such systems, the system comprises a plurality of templates, each template including anticipated events in a different patient health journey; and/or the template is based upon analysis of the aggregated member-specific contributed data indicative of events of other contributing members on the same patient health journey; and/or the template is based on contributed data from members who may have a similar condition or symptoms; and/or the follow-up communications based upon the template relate to a patient health journey initiated by a birth; and/or the follow-up communications based upon the template relate to a patient health journey initiated by symptoms or conditions indicated by the patient-specific contributed data; and/or the follow-up communications based upon the template relate to a patient health journey initiated by a diagnosis indicated by the patient-specific contributed data; and/or the follow-up communications based upon the template relate to a patient health journey initiated by a treatment plan indicated by the patient-specific contributed data; and/or the follow-up communications based upon the template relate to a patient health journey initiated by identification of a physical condition potentially detectable from the aggregated member-specific contributed data; and/or the follow-up communications based upon the template relate to a patient health journey initiated by identification of a new treatment of a physical condition detectable from the aggregated member-specific contributed data; and/or the follow-up communications based upon the template relate to a patient health journey initiated by identification of a new examination or test useful in determining a physical condition detectable from the aggregated member-specific contributed data; and/or the follow-up communications based upon the template comprise a custom report adapted to facilitate a contributing member consulting a medical professional; and/or the follow-up de-identified communications comprise recommendations for acquisition of additional data of the respective contributing members; and/or the member-specific contributed data comprises health-related data, and the recommendations comprise at least one physical examination or test related to physical condition of the respective contributing members; and/or the processing circuitry analyzes the member-specific contributed data of each member to determine at least one most convenient and/or cost effective source for the acquisition of additional data, and the recommendations include an indication of the most convenient and/or cost effective source for each respective recommendation to each respective contributing member; and/or the processing circuitry re-evaluates the member-specific value after receipt of follow-up member-specific contributed data from each respective contributing member; and/or the follow-up communications comprise an indication to each contributing member of the re-evaluation of the member-specific value applicable when the respective contributing member contributes the follow-up member-specific contributed data; and/or the processing circuitry transfers an asset amount to each member-specific account based upon the member-specific value; and/or the user-specific value is attributed as a currency and/or a cryptocurrency and/or an ownership share in the database; and/or the processing circuitry is configured to make ledger entries in an immutable and/or cryptographically encoded ledger and/or a blockchain based upon interaction with the contributing members. Methods, including computer-implemented methods may be implemented to utilize such techniques, including any of the specific variations mentioned above.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
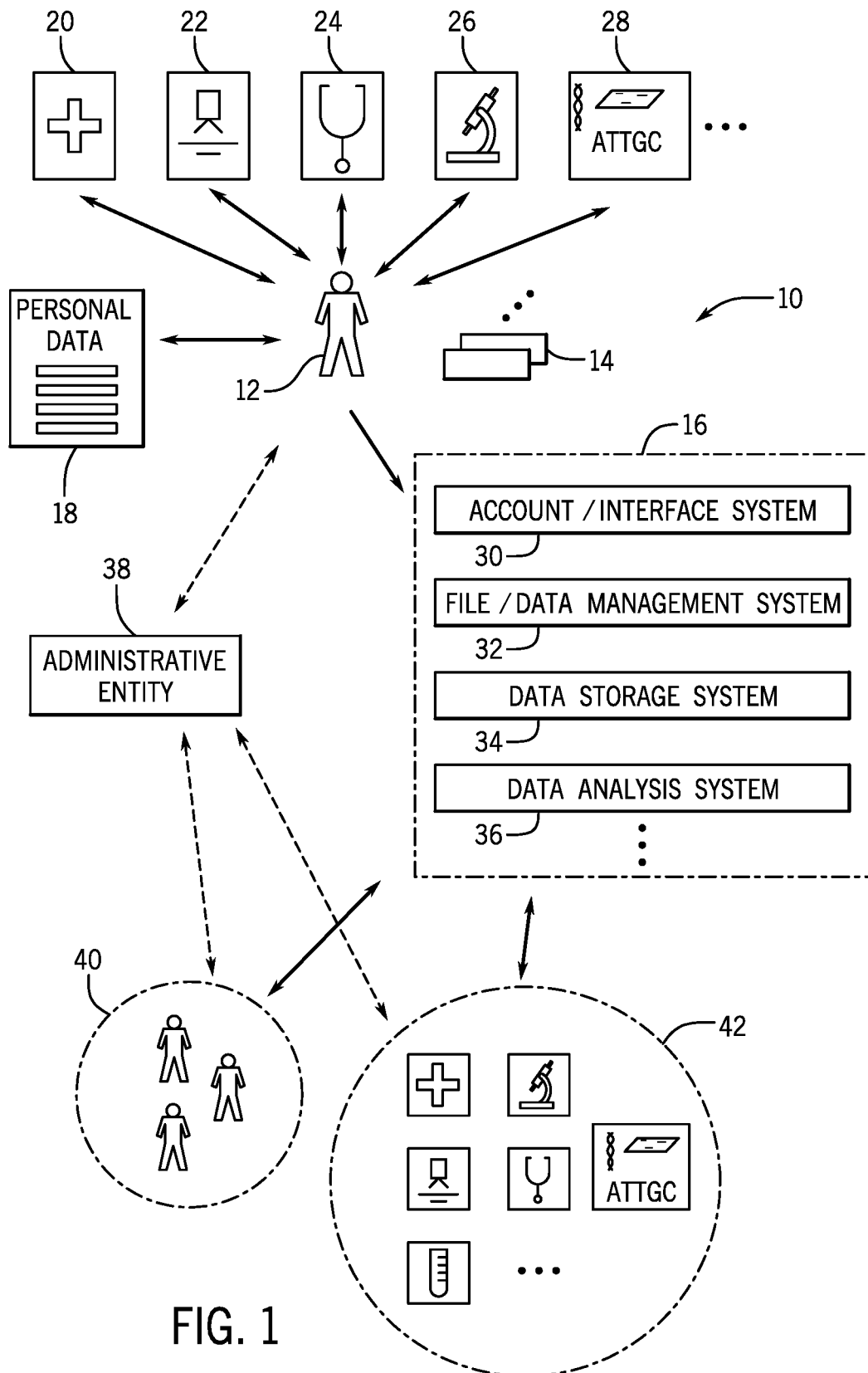
FIG. 1 is a diagrammatical representation of an example platform for the contribution, analysis, aggregation, and management of member data.

SYSTEM AND METHOD OVERVIEW: The present disclosure relates to technologies disclosed in international patent application number PCT/US2018/061419, filed on Nov. 16, 2018 by LunaPBC, and entitled "PERSONAL, OMIC, AND PHENOTYPE DATA COMMUNITY AGGREGATION PLATFORM", which is hereby incorporated into the present disclosure by reference in its entirety and for any and all purposes.

The inventions disclosed here aim to build systems, platforms, processes and technologies for collecting contributed data from members of a community, compensating such contributions, and providing enhanced quality of the data along with novel uses. The unique and novel methodologies are scalable, and maintain privacy, while moving towards more complete and accurate data of many types and sources.

In accordance with some aspects of the disclosure, solution to the data collection, compensation, aggregation, completion, and accuracy problems may involve several steps or phases. First, computer assisted techniques are used, which may employ machine learning or similar algorithmic methods to identify missing data components. For instance, it is possible to identify when individuals visit a health care provider for a specific condition and to identify a diagnosis of a professional and a corresponding treatment recommendation. Using this information the software can then search out whether information exists on the patients adherence to the treatment along with treatment results short term and long term. Automatic identification of this missing information using algorithms, computers, or other logic-based approaches may be the first step in the process.

The system can also identify when a healthcare provider did not use a digital entry field and instead used a freeform comment field. One initial step could be to simply digitally analyze the comments and attempt to translate comments, possibly using natural language processing, into digital database field entries. In some cases the system would not be able to parse comments or interpret manual entries. In these later cases a person may be needed to read the manual entry and provide interpretation. In some of these cases, automated communications, questions, customized surveys and the like could be generated and sent to the contributing member of the community to complete, provide, or correct any submitted data.

Another source of missing information could be during the formation of disease cohorts. It would be possible to identify factors common among the case cohort and to rate or analyze the information with respect to a candidate or control cohort. In these cases the statistical power of the study would be increased if missing information from a subset of cohort members was able to be addressed and added to the study.

Also, the system could automatically compare member conditions, symptoms, or reported diseases with those of other community members, assemble members into virtual cohorts around diseases or conditions, and then identify possibly important information contained in other member records but missing from the records of other members in the virtual or candidate cohort. The missing information could be an analytical test, imaging modality, or questions regarding health environment or quality of life.

Solutions to fill in information gaps may include techniques such as utilizing machine learning, data imputation from a large datasets, and/or the automated creation and distribution of custom user surveys. For example, when PROs are identified as missing from the record, the system would review all the existing data records of an individual associated with the condition in question, including reported symptoms and prescribed treatment. Based on this information, a custom survey could be created to retrieve information, such as whether the individual followed the treatment and whether the symptoms were resolved or new symptoms are emerging. This survey could be time-based if the condition is current, or retrospective if the condition is based on past medical history.

Another solution for addressing gaps in PRO information would be to query the database, such as to assess whether the records show the purchase of prescriptions prescribed by the healthcare professional, whether future health records reveal information on the listed symptom, or whether information on the condition could be imputed from other records in the database. Following these examples, for instance, when gaps in EHRs are identified due to missing fields, or conflicting information exists in the records a custom survey could be generated specifically to fill the gaps, and the survey could be sent out to the individual.

Many uses may be made by analyzing member-specific contributed data, as well as aggregated data from many members. For example, the system itself or members of the community may initiate or carry out self-assembly of de-identified community members into cohorts around diseases or other important issues (e.g., health, treatment, lifestyle, legal, etc.). In some use cases, members of the community may want to search out other members with similar chronic or acute diseases. A value in the short term may be for members to share information with each other to solicit suggestions on what may or may not help in alleviating the condition in question. A long term value may be the internally driven creation of narrow disease (or "condition" or "situation") cohorts that could be leveraged for future discoveries of links, such as between disease and the genome, microbiome or other social determinants of health. This discovery would be made possible by the initial self assembly of the cohort, the identification and retrieval of potentially relevant missing information, and the use of tools to identify correlations that exist in the case group but may be rare in a control group.

One important challenge is the enabling of members to come together and communicate while also protecting their anonymity. It will be possible to use the disclosed platform to enable members to search each other out based on phenotypic or genomic signatures, or other data types (e.g., disease or condition diagnoses, symptoms, demographics, geographic information, ethnicity, employers, life history, etc.). Members could then anonymously send out invitations or e-mails to other members requesting they connect in an internal chat room or join an internal group, for example. Once in a group, members could communicate information related to a specific disease or condition and determine whether others in the group share the condition. They could also then identify missing information and trigger a request to fill out a survey or to pursue an analytical test by an external professional, for example. Results could be uploaded and compared to further refine a cohort. Continuous queries could be generated to identify unique genomic or phenotypic correlations associated with the disease or condition in question. A reliable platform to seek out other members based on disease condition, communicate with other members, request retrieval of important missing information, and search for discovery links is invaluable and not possible today.

One underlying premise behind the present techniques is that a community ownership plan creates a people-driven scientific enterprise perceived as one worth joining, and based upon the premise that the best way to encourage new contributors to join and broadly consent to the use of their data is to make them full and engaged partners in the project. This may imply databases that will be 100% owned, or partially owned by data contributors, who will gain increased stakes as they contribute genomic data, phenotype data, health, and other personal data of interest. Unlike other approaches in the field, proceeds generated by providing access to the data (for instance to pharmaceutical companies) will be apportioned among the community based on for instance total and types of contributions to the community. Furthermore in order to provide contributors control over their data, contributors will have the ability to withdraw consent by returning their original stake or a stake of commensurate value at any point.

Aside from a formal stake in the enterprise (sometimes referred to in the present disclosure as "the system"), partnership may also mean seeing the studies and the results of such studies that are performed, and having the opportunity to provide feedback on what is happening with the database. For many participants, a primary motivation will be to support the greater good through scientific discovery. The system or the system administrator or sponsor may aim to encourage this type of participation through regular communications to build trust in the management of the database, and its contributions to science.

Community ownership solves many of the problems of trust and data control that act as obstacles to participation in biomedical studies, but for it to be effective the mechanism of ownership cannot itself become an obstacle. Encrypted databases, cryptographic ledgers, and representations of ownership stake, such as cryptocurrency coins and similar devices may provide a straightforward and hassle-free means to implement decentralized and large scale ownership. After making their initial data contribution, participants may earn additional participation, ownership, coins, etc. (sometimes collectively referred to in the present disclosure as "value") for contributing additional data.

A useful goal may be to identify the molecular basis of disease, causes of a chronic disease, or social determinants of disease, even if the economics are insufficient for commercial organizations to underwrite the efforts. In such cases the system could partner with nonprofit organizations.

One long term goal may be increasing the value of the "coins" or "value" attributed to data contributors (sometimes referred to in the present disclosure as "members") by maximizing the value of the database. This goal will incentivize members or collaborators to partner with all players in the ecosystem even at the expense of short term profits (e.g., partner of choice in the full ecosystem). It will also align goals with those of the member community (i.e., focus on the intrinsic benefits and intangible satisfaction of solving life's most important problems).

In some embodiments, new data contributors may receive a digital "wallet ID" and a custom cryptocurrency coin, that is designed to represent or track the value of the database asset, every time they contribute additional data. A wide range of genomic and omic data types may be accepted, including for example SNP array data, DNA sequencing data, somatic genome data, methylome data, virome data, pathegenomic data, and microbiome data. High-quality health, medical, and environmental data may also be accepted, including electronic medical records, surveys on diet and exercise, health history, and data from wearable devices, and personal and/or demographic data that might prove insightful for research. (It should be noted that in some embodiments, and for some uses, even lower quality or weaker data may be very helpful, such as for large scale studies and where other data is available to complete or complement such data.) Environmental data may also be accepted such as water quality, weather, air quality, and other data relating to an individual's exposome. The exposome can be defined as the measure of all the exposures of an individual in a lifetime and how those exposures relate to health. The database(s) may also accept data pertaining to non-human subjects and organisms, including animals, plants, microbes, viruses, fungi, or even "environmental" data such as to determine all possible organisms present.

In certain disclosed embodiments, the system calls upon a server that, in operation, serves interface pages to contributing members of an aggregation community for receipt of member-specific account data and member-specific contributed data. The member-specific contributed data may comprise any of a vast range of data types. A database is maintained by an administrative entity that, in operation, stores and aggregates the member-specific contributed data with member-specific contributed data contributed by other contributing members. Processing circuitry maintained by the administrative entity processes member-specific account data received from the contributing members via the interface pages to establish member-specific accounts based on the member-specific account data, and attributes a member-specific value to the member-specific accounts based upon respective member-specific contributed data.

The contributed data is subjected to one or many forms of analysis to determine its completeness and accuracy (sometimes more broadly referred to as its "quality"). Where possible, the data entries or fields may be automatically completed or corrected. Additional data may be solicited from the members, and communications may be made on the basis of identified quality issues. But many other communication initiators may be contemplated, such as based upon anticipated "pathways" or "journeys" of the members, such as through life, through treatments, through disease discovery, diagnosis, and management, and so forth. The analysis may, in fact, be continuous, periodic, or episodic. It may be based, for example, upon recognition of a possible condition or life-improving activity that becomes apparent from the contributed (and aggregated) data. Recommendations for acquiring or providing additional data may be made that can improve the accuracy or certainty of determinations of the conditions (e.g., a diagnosis, preventative measures, etc.). A number of the possible processing and use cases are discussed in this disclosure.

In certain of embodiments, the processing circuitry attributes the member-specific value based upon a pre-established calculation applied to all contributing members. An asset value or amount may be transferred or applied to each member-specific account as consideration for member-specific contributed data of the respective contributing member. By way of example, an asset amount may be calculated by a formula having a generalized form:

$$F=x/y;$$

wherein F is the fraction of ownership; x is the sum of ((W1)×(sum of data units of a first type of data unit)+(W2)×(sum of data units of a second type of data unit)+(W3)×(sum of data units of a third type of data unit) . . . +(Wn)×(sum of data units of an n type of data unit)) associated with the account; y is the sum of ((W1)×(sum of data units of the first type of data unit)+(W2)×(sum of data units of the second type of data unit)+(W3)×(sum of data units of the third type of data unit) . . . +(Wn)×(sum of data units of the n type of data unit)) associated with all accounts; and W1, W2, W3 . . . Wn are optional weighting factors, and/or the database is configured to store member-specific contributed data of different types. In such embodiments, the processing circuitry may attribute the member-specific value based upon types of member-specific contributed data submitted by each member, and the quality of the data. As mentioned, many different data types may be involved, such as (and many of these are super- or sub-sets of one another, or overlap one another): omic and phenotype data, health data, personal data, familial data, environmental data genomic data, microbiomic data, epigenomic data, transcriptomic data, proteomic data, genotype data, single nucleotide polymorphism data, short tandem repeat data, microsatellite data, haplotype data, epigenomic data, genome methylation data, microbiomic data, whole or partial gene sequence data, whole or partial exome sequence data, whole or partial chromosome data, whole or partial genome sequence data, medical record data, exercise data, dietary data, and wearable device data. In some embodiments, the database is configured to separately store member-specific contributed data for a respective member personally, an animal, plant, or microbial species owned or controlled by a respective member, and an environment owned or controlled by a respective member.

In some embodiments, limited access to member-specific contributed data and/or aggregated data may be offered to third-parties, such as on the basis of contractual arrangements with the administrative entity of the system, and any remuneration from such activities may flow back to the contributing members. It is contemplated that only de-identified contributed data will be accessed based on third-party submitted study design criteria. These criteria may be used to query the system's database(s) for appropriate information to include in a possible study. The relevant data is only identified based on a unique identifier independent from member personal information (that is, in a de-identified manner that does not permit personal identification of the members). Once subsets of information are identified, the information may be aggregated and populated in a secure, private logic-controlled "sandbox" within the system's secure cloud service site for analysis by third-parties who may be interested in analysis, tests, studies, and research based on the aggregated member data. In some situations (i.e., clinical trial recruitment), the third-party may be interested in contacting members directly. The system may enable this via an anonymous process that leverages the unique identifier associated with the members' data, which allows the third-party to invite members into a direct communication (but in present embodiments the third-party still has no knowledge of the members' personal information). It is then the members' choice whether they will engage in direct contact with the third-party or not. Preferences to receive these invitations can be turned on or off within a profile page of each member's account. All information in the system only includes what members voluntarily authorize to share.

Moreover, at any time, members can choose to delete some or all of their shared information from the system, and withdrawal of information will impact the member's ownership or value stake in the system. In all events, the member is the owner of their data.

In some embodiments, the system may provide training or educational materials to members, which may assist in the acquisition and contribution of higher-quality data, the completion of contributed data, and the correction of such data. Educational materials may include, for example, videos, textual presentations, exercises, and so forth, and may be structured as modules that members may progressively access to better understand both the workings of the system, their options in the system, and more broadly, any aspect of the data contributed, its use, its benefits, any recommendations made, any cohorts determined, and so forth. In some cases, the shares, value attributed, or some other form of compensation may be linked to the completion of stages in such educational materials.

TERMS AND CONCEPTS: Through the present disclosure, certain terms and concepts are referred to in embodiments of the technology described. These may be understood by their ordinary and customary meaning in the art, and in view of any special meaning used in the present context, as will be understood by those skilled in the art. Some of the terms and concepts include:

Data
  member-specific account data: information relating to a members residence, contact info, tax filing number, ownership stake, birth date, etc.;
  member-specific contributed data: personal, health, medical, environment, historic, and omic data that is specific to a person contributing the information;

data: depending upon the context, the general term data may apply to account data, contributed data, data based upon one or both of these, or to processed and/or aggregated data;

data derived from contributed data: metadata, summarized data, or data emanating from a logical or mathematical analysis of the member data;

medical data: electronic medical and health records, results of tests either analytical or subjective, medical diaries, prescriptions etc.;

health data: data relating to the health, wellbeing, and quality of life including sensor data, biometric data, diet tracking, survey answers related to health, quality of life, family status, emotional state or condition, health diaries;

personal data: data relating to an individual's behaviors, habits, and daily activities such as geographic locations visited, purchasing or spending activities, web browsing, friends, social media posts, employee record, academic records, etc. (in general, this may include any or all data relating to an individual, including genomic, health medical, etc.);

familial data: family history including health and medical history, lineage, and genealogy;

environmental data: envirome and exposome data encompasses a) all of the environmental conditions required for successful biological life that affect human health, and b) life-course environmental exposures (including lifestyle factors), from the prenatal period onwards, including quality and chemical, omic, or organic content of air, water, climate, and soil;

genomic data—relating to the make-up of an individual germ-line DNA and data related to somatic mutations including cancer DNA information, typically all cells in an individual's body contain the same genomic data with only minor variations, but not always;

microbiomic data: relating to the nucleotide sequence or taxonomic classification of other organisms that exist symbiotically, parasytically, or commensal with an individual; common locations of these communities are hand, sinuses, mouth, gut, rectum, sex organs, etc.; also included is pathegonomic and viromid data, covering deleterious microbes, fungi, and viruses;

epigenomic data: relating to genomic data that impacts the expression of a person's genome from DNA sequence data to proteins, including for example DNA methylation, histone wrapping, etc.; epigenomic data can be different cell to cell in the body and tissue type to tissue type;

transcripomic data: the set of all RNA molecules in one cell or a population of cells, often with expression level values included;

proteomic data: a list of proteins occurring within a cell or group of cells, often with relative abundance values;

pathogenomic data: genomic data and/or phenomic data on pathogens that affect human health; however, studies also exist for plant and animal infecting microbes. These pathogens may include bacteria, viruses, and fungi.

genotype data: relating to determining single nucleotide polymorphisms "SNPs" or single basepair difference between individuals (e.g., A, C, T, G), data sets often including insertions of a single base and deletions of a single base when discussing consumer genomic genotyping data results;

single nucleotide polymorphism data: a variation in a single nucleotide that occurs at a specific position in the genome, often called "SNPs";

short tandem repeat data: a short tandem repeat is a microsatellite, consisting of a unit of two to thirteen nucleotides repeated hundreds of times in a row on the DNA strand;

microsatellite data: a microsatellite is a tract of repetitive DNA in which certain DNA motifs (ranging in length from 1-6 or more base pairs) are repeated, typically 5-50 times;

structural variants: a region of DNA approximately 1 kb and larger in size and can include inversions and balanced translocations or genomic imbalances (insertions and deletions), commonly referred to as copy number variants (CNVs);

haplotype data: a set of DNA variations, or polymorphisms, that tend to be inherited together. A haplotype can refer to a combination of alleles or to a set of single nucleotide polymorphisms (SNPs) found on the same chromosome;

genome methylation data: a list of bases or sets of bases that have been methylated, a process where methyl groups are added to DNA base;

whole or partial gene sequence data: a succession of letters that indicate the order of nucleotides forming alleles within a gene;

whole or partial exome sequence data: a succession of letter that indicate the part of the genome composed of exons, the sequences which, when transcribed, remain within the mature RNA after introns are removed by RNA splicing and contribute to the final protein product encoded by that gene;

whole or partial chromosome data: a succession of letter that indicate the sequence of whole or part of a chromosome;

whole or partial genome sequence data: a succession of letters that indicate the order of nucleotides forming alleles within a DNA (using GACT) or RNA (GACU) molecule;

medical record data: a patient's individual medical record data identifies the patient and contains information regarding the patient's case history at a particular provider; the health record as well as any electronically stored variant of the traditional paper files contain proper identification of the patient;

exercise data: covering any activity, or lack thereof, requiring physical effort, carried out especially to sustain or improve health and fitness;

dietary data: pertaining to nutritional status, calories consumed in order to cross-sectionally describe dietary patterns of consumption and food preparation practices, and to identify areas for improvement;

wearable device data: devices that can be worn by a consumer and often include tracking information related to health and fitness; other wearable tech gadgets include devices that have small motion sensors to take photos and sync with your mobile devices;

biometric device data: include any device that tracks biometric data, from heart rate monitors to state-of-the-art ingestible and/or insertable sensors that can provide your granular data about the interworking of your internal systems;

data indicative of at least a portion of the respective member-specific contributed data: some or all of the contributed data may be processed and derived data may be kept, stored, analyzed, etc.; indicative data may include various processed or encoded forms (e.g., tags, structured data, etc.);

structured data or files derived from the received and stored member-specific contributed data: depending upon the processing and analysis, structured data, including tagged data, metadata, etc., may be created based upon raw or partially processed data contributed by members;

low-pass sequencing: a succession of letters that indicate the order of nucleotides forming alleles within a DNA (using GACT), typically gathered at a sequence redundancy that is not sufficient to assemble an individual's full genome, region of the genome, exome, gene, or chromosome, but is sufficient to identify genotypes or minor structural variants within the genome, gene, chromosome, or exome;

personally identifiable information: information that can identify the member, either alone or in combination with other information;

Information gap, incomplete data, missing data: data that is either not present at all, or that can be improved and/or can be refined to enable or enhance statistical correlations (e.g., obtain an improved P value) and/or confidence levels for such correlations between data of the same member, data between members, aggregated data, between member data and aggregated data, or between any of these and reference data, to make or support findings, recommendations, decisions, and conclusions; in some cases such data may be insufficient in breadth, depth, and/or scale;

incorrect or erroneous data: data that is present, but factually wrong or that appears to be inconsistent with other data (of the same or a different type);

Actors member: any person who contributes data that is aggregated and who receives a value for the contributed data;

administrative entity: a company or entity apart from the members and from third-party users of the aggregated data, which interfaces with members to receive data used to create member accounts, and receives, processes, and aggregates the contributed data, and then makes the aggregated data available to third-parties, such as for research and analysis;

third-party: a person or entity apart from the members and from the administrative entity that has an interest in the aggregated data and that interacts with the administrative entity to perform operations on the aggregated data, such as searches and analysis, and who provides remuneration to the member community in cooperation with the administrative entity (third-parties may include, for example, pharmaceutical companies, research institutions, universities, medical institutions, governmental and quasi-governmental institutions, independent researchers, and so forth);

successor in interest to the respective member: a person or entity who obtains legal rights to the data of a member (e.g., through an estate);

data users: institution, researchers, foundations, or individuals who search or query the aggregated data;

cohort: a grouping of contributing members based upon one or more factors detectable in contributed and aggregated omic and phenotypic data, such as a physical condition, a diagnosis, geographic location, a family situation, a predisposition, a patient journey, and so forth; in determining cohorts several other factors, data types and data combinations may be considered (e.g., demographic data, personal data, geographic data, omic data, employment data, health history, lifestyle, habits, interests, etc.);

System Components/Subsystems database: one or more databases, typically maintained by the administrative entity, and containing member data, metadata, data derived from member data, structured data, etc. (databases may be constructed in conventional manners or by specific technologies, such as blockchain);

processing circuitry: one or more digital processors typically embodied in one or more computers, servers, dedicated processing facilities, etc.;

cryptographically encoded ledger: a ledger that is encoded to permit access by cryptographic methods (e.g., based on private and/or public keys);

immutable ledger: a ledger that cannot be changed, or that cannot be changed without the change being evident;

blockchain: a growing list of records, called blocks, which are linked using cryptography; each block contains a cryptographic hash of the previous block, a timestamp, and transaction data; by design, a blockchain is resistant to modification of the data;

centralized database: a searchable data store including a centrally located database, virtual centralized database, cloud based database, collection of dis-aggregated databases that are purpose built for the respective data types, or other infrastructure having the ability to aggregate data; for the present purposes, such "centralized" databases may also include "federated" databases, including databases physically located and maintained in different locations (e.g., some countries or jurisdictions may require local or otherwise controlled storage for their populations, smart phones and other networkable devices may individually contain databases that are or may be federated);

account database: a database, typically maintained by the administrative entity that stores member account data, which may include member-identifying data and data related to ownership of databases and/or value attributed to a member;

contributed data database: a databased that contains de-identified and/or encrypted data contributed by members; the data of the contributed data database may be any type of data mentioned above, for example;

account blockchain or distributed ledger protocol: consensus protocol; a process, encoded in software, by which computers in a network, called nodes, reach an agreement about a set of data;

contributed data blockchain or distributed ledger protocol: a protocol that utilizes blockchain and/or distributed ledger technologies for receiving, processing, aggregating and storing contributed data;

universal resource identifier protocol: a Uniform Resource Identifier is a string of characters that unambiguously identifies a particular resource; schemes specifying a concrete syntax and associated protocols define each URI;

data key: a digit or physical key which holds a variable value which can be applied to a string or a text block, in order for it to be encrypted or decrypted;

data key for each member-specific account is stored in an encrypted manner;

one-way pointer: a programming language object that stores the memory address of another value located in computer memory;

secure alternative authentication protocol that maintains a de-identified nature of the stored member-specific contributed data;

secure alternative authentication protocol comprises accessing a contact address for the respective contributing member;

secure sandbox memory: a virtual space in which software can be run securely and logic can be applied to control queries and query responses;

secure cloud service site: a platform of servers, whereas your virtual sites live on multiple computers, eliminating any single point of failure; such sites are secure, and ultra-reliable, and generally always online;

educational interface pages: interface pages and materials that may be served to members for educating the members of the workings of the community system, the details and types of data that may be contributed, the details and types of value that may be obtained by joining and participating in the community, as well as to better educate members regarding such things are how to improve data quality, how to maintain accurate and up-to-date data, etc.;

segregated data key: data is separated such that accessing one portion of a record does not automatically allow access to other portions of the record;

segregation data key database: a structured set of data that contains key (a variable values that is applied to a string or block of text to encrypt or decrypt it) that is used to encrypt or decrypt data;

patient journey or patient health journey: a series of stages or events relating to the life, health, or activities of a member ("patient"); such patient journeys may relate to a disease or treatable condition, while in other cases it may imply some portion or aspect of the member's life (e.g., normal care stages following birth, vaccinations, eye care, regular checkups, regular monitoring, diet management, etc.);

template: an outline of pathway that includes anticipated events likely to occur in a patient health journey; templates may be based upon analysis of the aggregated member-specific contributed data indicative of events of other contributing members on the same patient health journey, such as contributed data from members who may have a similar condition or symptoms;

artificial intelligence: programming or code stored and executable by processing circuitry to interpret data, to learn from such data, and to use those learnings to achieve specific goals and tasks through flexible adaptation;

machine learning: a process based on programming or code stored and executable by processing circuitry based on algorithms that may build a mathematical model of sample data, known as "training data", in order to make predictions or decisions without being explicitly programmed to perform the task (it may be noted that sometimes terms such as artificial intelligence, machine learning, and deep learning are used interchangeably);

survey: a communication, typically sent or made available to contributing members online, that includes or solicits inputs (e.g., fields) providing specific data from the members;

Value-Related Components member-specific accounts: accounts established for individual members that allow for contribution of data, management of member activities, accounting and tracking ownership and/or value attributed to a member, opting in and out of activities, etc.;

member-specific value: value attributed to individual members by virtue of their participation in the community, such as by contribution of data; value may be in one or more forms, including, for example, ownership shares, currency, cryptocurrency, tokens, etc.;

pre-established calculation: mathematical calculation or logic based calculation established and officially implemented prior to usage;

asset amount: an amount of something of value, typically referring to value attributed to members for their participation in the community;

currency: a basis of value, such as money or some other commonly recognized basis of transaction;

cryptocurrency: a digital currency in which encryption techniques are used to regulate the generation of units of currency and verify the transfer of funds;

member-specific value is at least partially based upon the quality evaluation: value may be altered (increased or decreased) based upon a quality, reliability, or similar determination (e.g., of the data, of a source of the data, of the contributor, of past interactions, etc.);

smart code: executable code that provides for defined steps or operations recorded in a verifiable manner (e.g., an immutable ledger);

a smart contract: a computer protocol intended to digitally facilitate, verify, or enforce the negotiation or performance of a contract (e.g., through the use of smart code);

educational module/video: educational materials that may be provided (e.g., served) to members in a desired sequence to systematically lead the members through an instructional program;

third-party interface: pages or other materials that may be served to third-parties to allow for activities such as the establishment of accounts, requests for studies and searches of aggregated data, conveyance of value (e.g., remuneration) for such activities, and potentially for contacting members for follow-up activities (e.g., clinical studies);

Operations aggregate data: data combined from several measurements and/or inputs; when data are aggregated, groups of observations are replaced with summary statistics based on those observations;

attribute value: to cause value to be created and recognized;

transfer remuneration/currency/value: attributed or recorded compensation of a defined sort, such as in a member account;

separately store (data of different types): store and/or segregate data in different databases;

de-identifying member data (e.g., contributed data): data that has undergone a process that is used to prevent a person's identity from being connected with information; defined broadly to include any method or approach to protecting identity during storage and processing of data, including the use of homomorphic encryption on encrypted identifiable data, utilized to facilitate anonymous or blinded data queries, communications, etc.;

the administrative entity does not link member-specific contributed data to an associated member-specific account in a manner that would personally identify the respective contributing member;

sending data to the contact address without accessing the stored member-specific contributed data;

quality evaluation: a process used to determine the accuracy, veracity, and potential value;

quality scoring: applying a function or a look-up table in order to represent the quality of data;

determining inconsistency with member-specific contributed data;

sending a notice to a contributing member of results of the quality evaluation;

generating a report of results of the quality evaluation;

contributor evaluation: analysis of data and/or activities of members contributing data to determine aspects such as reliability that may affect the use of data contributed;

contributor scoring: a number or factor that may be generated based on contributor evaluation and that may be used, for example, in later interactions with the same member (e.g., as more or less "trusted") and/or that may affect a value attributed based upon contributed data;

evaluation of past data submissions: analysis of data, data sources, contributing members, and so forth based upon evaluation of historical interactions and contributions of the member;

evaluation of a third-party source: analysis of an entity that generated or processed contributed data, such as to determine data quality, completeness, reliability, etc. (such third-parties may include, for example, sequencing facilities, medical facilities, etc.);

processing of later member-specific contributed data is altered for trusted contributing members;

interacting of the respective contributing member with the educational interface pages;

completion of successive educational modules;

compensating contributing members based upon interaction by the respective contributing member with the educational interface pages;

accessing to the aggregated member-specific contributed data without permitting third-party identification of members: activities between the administrative entity and third-parties to aid in analysis of aggregated data, such as for research and discovery without relating the aggregated data back to individual contributing members in a way that would identify the members;

remunerating by/from the third-party: transfer of value from entities interested in the aggregated data in exchange for activities such as searching, access, etc.;

stages of interaction by the third-party interface: progressive activities of establishing an account or relationship between the third-party and the administrative entity, arranging for remuneration for activities with the aggregated data, etc.;

third-party interface is configured to cooperate with the processing circuitry to perform searches;

permitting communication by the third-party to contributing members without permitting third-party identification: following analysis by a third-party, allowing certain contact (e.g., via email) between the third-party and contributing members (e.g., for invitation to clinical trials) in a way that does not provide the third-party with the actual identification of the contacted members;

third-party communicating based upon a unique identifier associated with the aggregated member-specific contributed data of the contributing members: similar communication but based upon technologies where the members are associated with identifiers that do not allow for personal identification of the members;

opting-out of communication from the third-party: an operation that a member may perform (e.g., via interface pages) to preclude being contacted by third-parties;

attributing a value to at least some of member-specific accounts based upon remuneration provided by the third-party for access to the aggregated member-specific contributed data: channeling of value (e.g., remuneration) based upon interest in or use of member data by third-parties, typically through the intermediary of the administrative entity;

attributing the value to at least some of the member-specific accounts based upon remuneration provided by the third-party;

attributing a value is based upon whether the respective member-specific contributed data corresponds to criteria provided by the third-party: may relate to specific remuneration or channeling of value to certain members whose contributed data is of particular interest to a third-party;

selecting a portion (for sandbox) of the aggregated member-specific contributed data for access by the third-party: down-selecting some data from the aggregated data that meet criteria of a third-party, such as resulting from a search;

segregating data: data for a given individual being segregated across several databases to increase security; each database has a different key for the individual so information cannot be combined without having all of the keys for an individual (stored in the segregation key database).

DESCRIPTION OF EMBODIMENTS: Turning now to the drawings, FIG. 1 illustrates an example data aggregation and management system 10 at the service of a member population made up of human members 12. The member population may be thought of in some respects as "users" to the extent that they will interact with the system via served interfaces both to create accounts, to contribute data, and to manage aspects of their account and data. They will typically comprise human contributors made up of individual members who may create member accounts and contribute data (typically about themselves) as set forth in the present disclosure. The data contributed may also include various populations or types of organism for which members may have data, including, without limitation, animal populations, and other populations (e.g., plants, microbes, environmental areas such as water and earth sources).

The system allows for data, files, and records 14 to be accessed, and uploaded for processing and aggregation of their content. In the present disclosure, contributed data may be referred to simply as "data" or "files" or "records" interchangeably. As discussed in the present disclosure, provisions are made for de-identifying the data contributed, that is, for removing the ability to relate the contributed data back to an identity of the contributing member, unless the member desires and consents to such identification. Management of the data, the account, and coordination of value attribution is by the system administrative entity 38 (i.e., the aggregation administrator or coordinator). The administrative entity may maintain a platform or system 16 itself having a number of components and systems as discussed below.

The contributed data may include genomic, or more generally omic data, medical data, personal data, including personal, family, medical and similar historical data, medical records, and any other data that may be of use in research and/or analysis of physical states or conditions of the relevant populations. These may be in the possession and/or control of the contributing member, or may be held in trust by various institutions, as in the case of files. In such cases, the members may access the files by physical or electronic transfer, or by any suitable means, or may simply make the data and/or files available to the system (e.g., via periodic, episodic, cyclic, or other transfer, such as from "wearable devices").

A wide range of individuals, institutions, businesses, and communities may create or assist in the creation of the data for each contributing member, and in many cases, the types of data, the completeness and/or correctness of the data may at least partially be a function of the originating source. The present techniques assist in completing and correcting contributed data, analyzing the data for quality, interacting with the contributing members to ensure high-quality data, and so forth. In the embodiment illustrated in FIG. 1, for example, the contributing member may themselves create or make available certain personal data 18, which could be provided via an online interface, form, template, questionnaire, or any other means. Moreover, various medical, governmental, quasi-governmental, health, and other institutions may create data, as indicated by reference numeral 20 (e.g., medical record data, hospitalization and treatment data, etc.). Similarly, imaging and lab institutions 22 may create image and related data. Medical offices and medical professionals 24 may create other health-related data (e.g., via regular or other visits compiled as patient medical records and the like). Pharmaceutical and research organization may create further data, as indicated generally by reference numeral 26. Omic data, including, for example, sequence data may be created by other contributors, as indicated by reference numeral 28. Many other sources of data may be envisioned as well, including wearable devices, home test kits and devices, personal electronic devices (e.g., computers, tablets, cellular phones), employers, just to mention a few. In general, the present techniques may focus on health-related data that may be useful to the contributing member or to others in the contributing community (or beyond), though that term should be very widely understood insomuch as many facets of the member's life may affect or be reflected in data possibly contributable by the respective member.

The system 16 provides a number of services, and these may evolve depending upon the organizational structure of the administering entity, and the needs and desires of the member community and third-party users. For example, in the illustrated embodiment, these may include an account interface system 30, a file/data management system 32, a data storage system 34, a value/share attribution system 36. Many other systems may also be present, or added, such as a third-party interface system that might allow third-parties to make use of the aggregated data, contact members, and so forth, such as for a fee.

In the illustrated embodiment, the members will typically interface with the system via a computer (or any other capable device, such as a tablet, smart phone, etc.). Data exchange will be enabled by any desired network connection, so that member data, account data, and contributed data/files 14 may be provided. Similarly, data exchange may take place, also by any desired network connections, with the contributing members or users making up the community, as indicated by reference 40, and with any other permitted third-parties 42. Ultimately, based upon the arrangements with these users, value will flow back to the administrating entity 38 and therethrough to the member community. Many forms of value may be provided, including monetary payments, cryptocurrency payments, ownership shares, and so forth.

As noted in the present disclosure, in some currently contemplated embodiments, interactions between the community members and the administrating entity may be based upon smart contracts, as are interactions with the third-party users. Moreover, the ownership and value attributed to the community members may be based upon one or more encrypted, decentralized, and/or public ledgers, cryptocurrencies, and so forth. Such techniques may allow for reliable tracking and "transparency" in transactions, while the present techniques nevertheless are based on confidentiality and member control of personalized or identity-permitting data and data associations.

Figure 2:
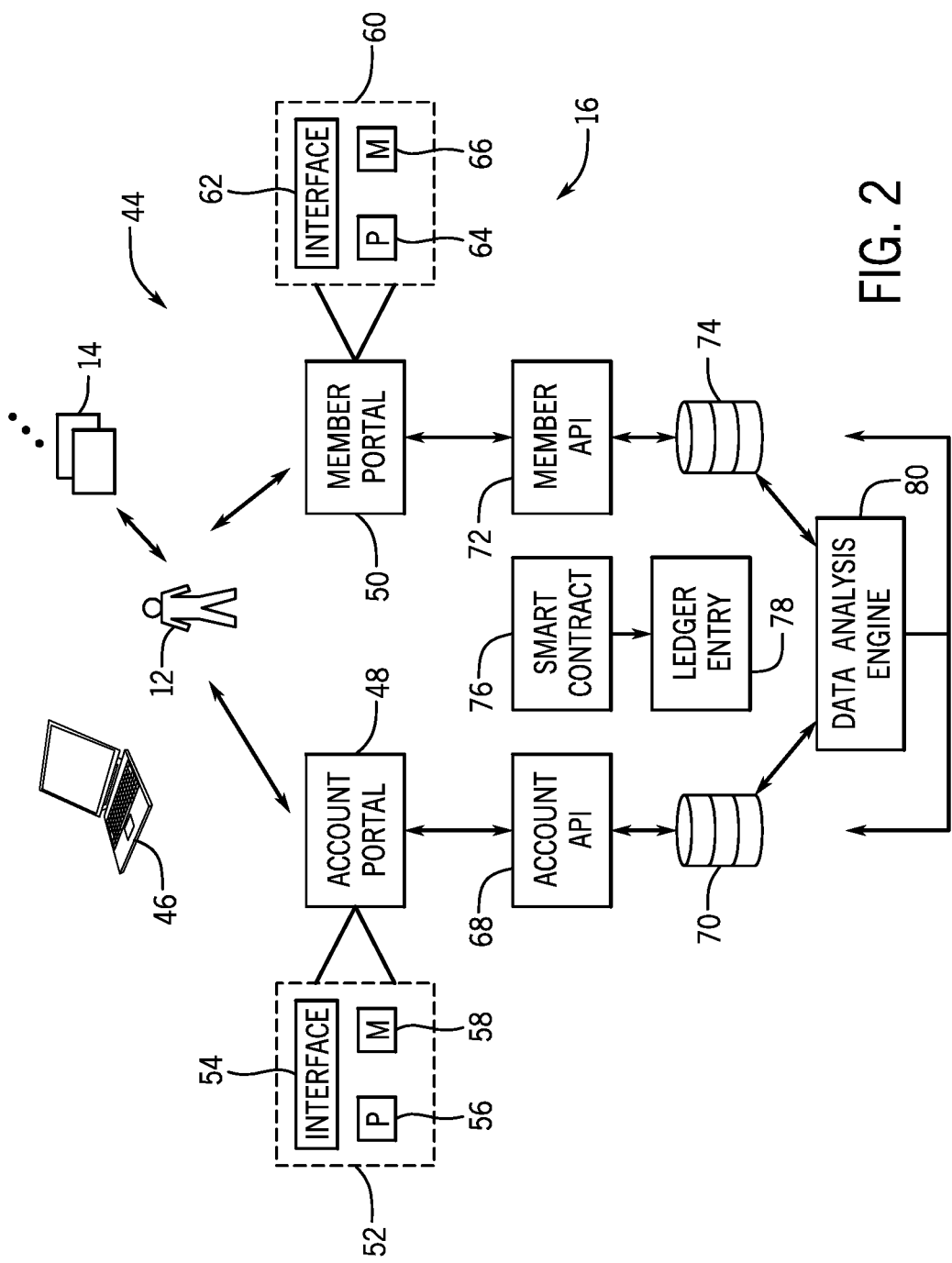
FIG. 2 is a diagrammatical representation of an example data and file contribution process.

FIG. 2 diagrammatically illustrates an example of account initiation and member interaction processes in accordance with certain presently contemplated embodiments. The process may begin with the member 12 interacting with a personal computer 46, or other device that can interact with the internet. Interface screens are served to the member computer by interacting system components, such as an account portal 48 and a member portal 50. The account portal is provided for interacting with the member computer in ways relating to the member account. As noted below, various approaches, protocols, and processes may be implemented to generate and account for value or shares in the database or databases of the present system. The account portal computer or computers 52 may include one or more interfaces 54 designed to permit interaction with the member computer as well as one or more processors 56 and memory 58. The memory will typically store various screens and interaction protocols that are implemented by the processor via the interface. The account portal may communicate again by any suitable network or combination of networks, and may operate based upon, among other things, a shares or account API 68.

The member portal 50, like the account portal 48, is maintained or overseen by the administrative entity of the system. The member portal itself may run on any suitable type of computer or combination of computers 60 and will be in communication with the member computer by the Internet or any suitable network or combination of networks. The member may contact the portal by a conventional URL, or by a browser search, or any other initial contact mechanism. The interface screens will walk the member through the account creation and data transfer process. As will be appreciated by those skilled in the art, the computer system running the member portal will typically comprise one or more interfaces 62 designed to allow for data exchange between the administrative entity site and the user computer. The interface 62 is in communication with one or more processors 64 and memory 66. The memory may store the interface screens, routines for generating the interface screens, routines for processing member data, and so forth, these routines being executed by the processor. The member portal 50 is in communication with and executed based upon a member API 72.

Data received, processed, analyzed, stored, and otherwise handled by the system, including both account-related data, member-specific contributed data, and aggregated data may be stored in one or more data storage systems 70 and 74. As discussed below, in the present context, these may be referred to as "centralized databases", meaning that they are available to the administrative entity for data access, analysis, searching, and similar operations. In practice, such databases may be physically stored in different locations, and may technically comprise "federated" databases, or any desired storage or data structure may be used.

As noted above, interaction with the administrative entity may be based upon one or more smart contracts as indicated by reference 76 in FIG. 2. Such smart contracts may detail and/or manage various interactions, stages of interactions, responses to interactions, and may keep reliable and traceable records of interactions with the members. In presently contemplated embodiments these interactions will be noted on ledger entries as indicated by reference 78 in FIG. 2. As also shown in FIG. 2, data storage devices or systems 70 and 74 (again, comprising one or more "centralized" databases) will make the member-specific contributed data, data derived from it, and/or the aggregated data available to a data analysis engine 80 which may examine the data to determine such factors as data quality, data completeness, data consistency, data accuracy, and so forth, but that may also analyze the data to determine possible follow-up with contributing members, possible "cohorts" of members who share one or more traits, conditions or issues, and so forth.

Figure 3:
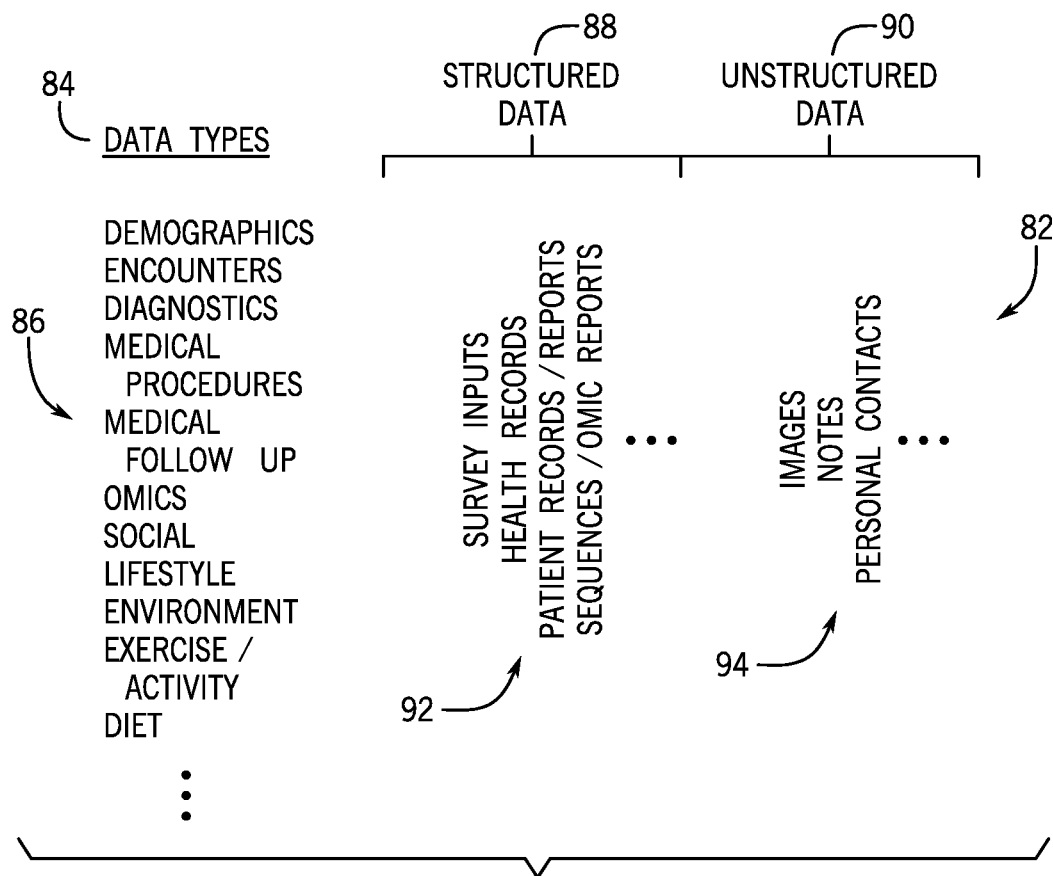
FIG. 3 illustrates various example data types that may be contributed and handled by the system and process.

FIG. 3 illustrates various example data types that may be contributed and handled by the system and processes. As noted, any of a wide range of data types may be contributed, processed and stored. It may be noted here that while reference is made in this disclosure to "types", in reality, many of these may be super- or sub-sets of one another, and in some cases, files and other collections of data may include several types. But for the present purposes, it is useful to consider these as separate types for many reasons, such as the fact that they often originate from different sources, they may comprise different file and data structures, they may be reported at different points in time, they may tend to include characteristic incompleteness and inaccuracies, they may be initiated at different times and in different ways, or simply because they may be thought of and handled by the members differently because of the underlying reason for their creation.

In the illustration of FIG. 3, data, generally referred to by numeral 82 may include different data types are indicated by reference numeral 84. These are illustrated as including different specific types of data 86, such as demographic data, encounters (e.g., between individuals, with environments, with pathogens, with diseases, etc.), diagnostic data, medical procedure data, medical follow-up data, omic data, social data, lifestyle data, environment data, exercise/activity data, and diet data—though clearly these and many other data types may be considered. In general, such data may be compiled, stored, and even contributed to the system as structured data 88, or unstructured data 90. In the illustration, the structured data is shown as including specific types of files or data 92, such as survey inputs, health records, patient records and reports, and sequence or omic reports. Here again, many other types of contributed data may be in a structured format. Other data which is unstructured may nevertheless be of keen interest, particularly when considered together with structured data, such as image data, physician notes, personal contact data, as well as many others. As noted in this disclosure, for example, lifestyle details, automatically detected data (e.g., from worn or home devices), and so forth may be structured or unstructured, and can still be handled by the system.

Figure 4:
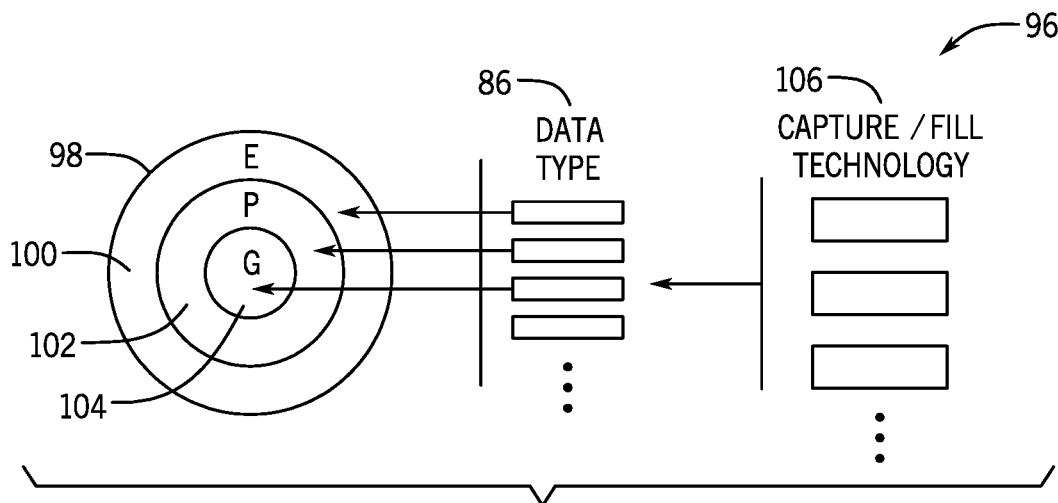
FIG. 4 illustrates analytical ways in which the data may relate to a contributing member.

FIG. 4 illustrates analytical ways in which such data may relate to a contributing member, and presents a different way to consider the contributed data. In this example, the relational structure 96 may correlate data 98 of an individual (or community) by, for example, data type and the one or more sources or methodologies for its creation and collection. In the illustration, the data 98 includes an environmental layer 100, a phenotype layer 102, and a genotype layer 104. Each layer may give rise to different data types 86 as discussed above, and these may be implied by the characteristics of the respective layer or layers (e.g., environment data may include encounters, geographics, demographics; phenotype data may involve ethnicity, physical characteristics, family details and history, personal data, and so forth; genotype data will typically include sequence data, etc.).

Moreover, each of these layers, and the corresponding data types may imply different data sources and capture methodologies 106. For the present purposes, it should also be pointed out that these are also mechanisms for filling in missing or incomplete data, for correcting erroneous or inaccurate data, and more generally for enhancing data by acquiring and contributing additional data. By way of example, such sources and methodologies may include medical visits, compilations of medical and health records, surveys and questionnaires (including online forms and interfaces), sequencing, imaging, wearable devices, home test devices, just to mention a few. Here again, these may produce structured or unstructured data (or both).

Figure 5:
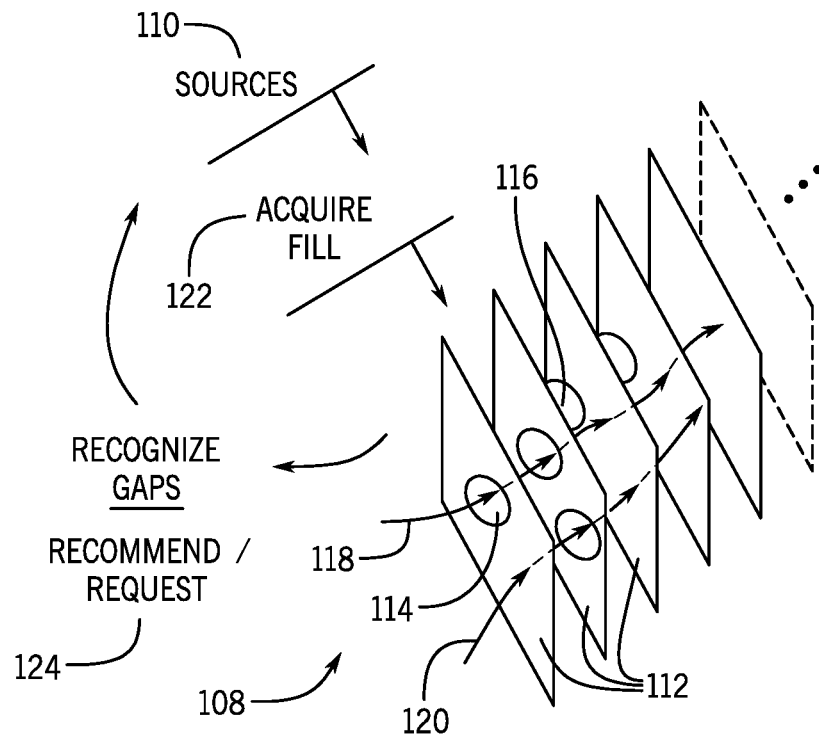
FIG. 5 illustrates different data types and ways in which gaps in data may be identified and filled.

FIG. 5 illustrates different data types and their interrelation, and ways in which gaps in data may be identified and filled, or incorrect or inaccurate data may be corrected. In this illustration, the data 108 originates from sources 110. The data may be thought of, similar to the depiction of FIG. 4, as different layers or data types 112. In most cases, the data contributed (or available) is not exhaustive in each layer or type, as indicated by the regions, holes or gaps 114 and 116 (which could also represent inconsistencies, inaccuracies, or low quality in the data). Such regions may be identified in a variety of ways. For example, analysis by the analysis engine of the processing circuitry disclosed may identify that certain fields or inputs are missing or inconsistent with one another in data of a particular type, or in data contributed at different times. In the illustration, moreover, conceptual or analytical pathways 118 and 120 through the data may reveal that useful parts of each layer or type are missing or inaccurate (or that a layer or type is missing entirely). As discussed below, the system may be able to automatically fill in the missing data, and such fill techniques may be based upon artificial intelligence, machine learning, simple comparison between similar data fields, and the like, so that the system is progressively refined and may require less communication with contributing members. In other cases, communications may be initiated with the members (including fully automated communications) to acquire or re-acquire data as indicated by reference 122. The requesting communications 124 may take the form of emails, customized surveys, requests, recommendations, and so forth. In presently contemplated embodiments, such communications are "de-identified" such that the administrative entity does not identify the contributing member by association with the contributed data.

Figure 6A:
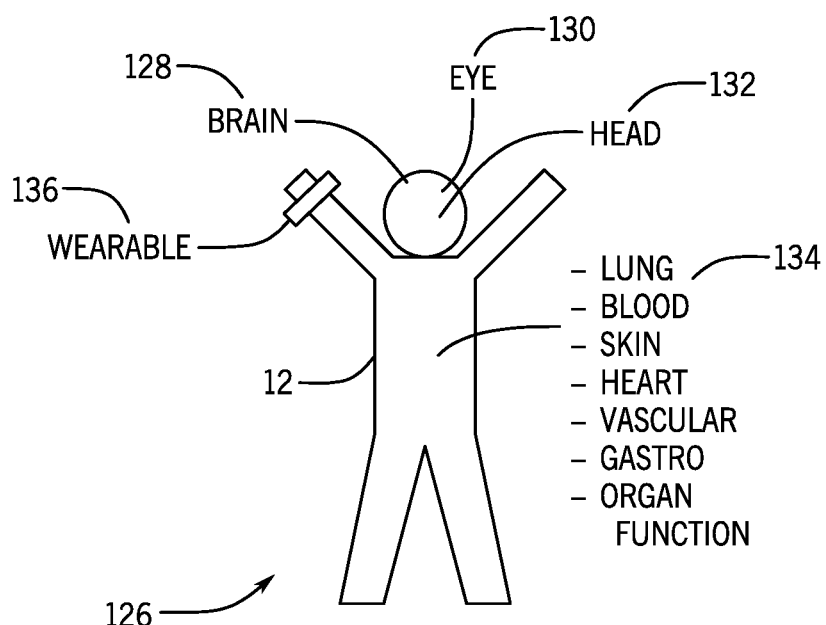
FIG. 6A illustrates certain data originating technologies for sensing or monitoring bio-related data for a member.
Figure 6B:
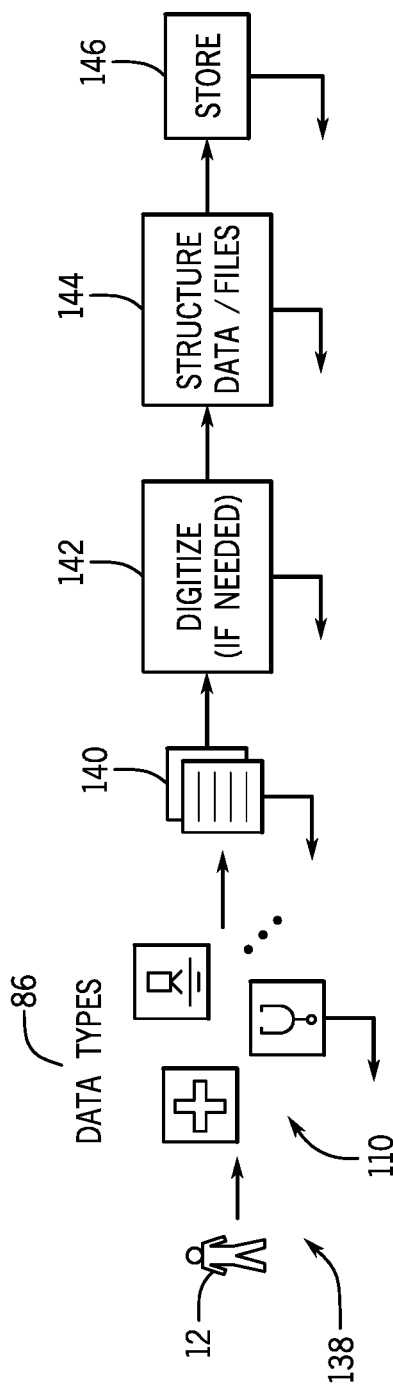
FIG. 6B illustrates an example data originating workflow, such as for medical-related data.
Figure 6C:
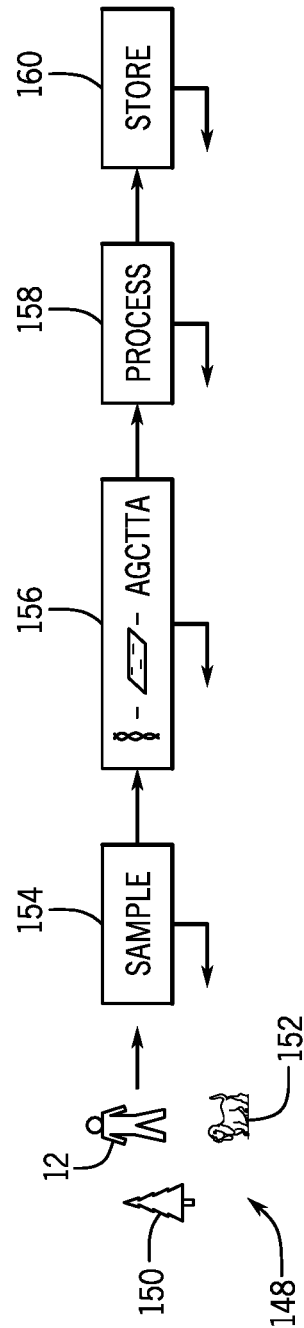
FIG. 6C illustrates another example data originating workflow, such as for omic data.

FIGS. 6A-6C illustrate certain example technologies or workflows for acquiring certain data types, and then for completing or complementing the data over time. FIG. 6A illustrates certain data originating technologies 126 for sensing or monitoring bio-related data for a member. These will typically be based upon the type (or sub-type) of data involved, and sometimes on the anatomy or physiological system from which the data is taken. For example, data may be collected relating to the brain 128 and brain function, typically from electroencephalograms (EEGs) and similar studies, but also from wireless mobile EEGs. Data pertaining to the eyes 130 may be collected by medical exams, eyeglass prescriptions, medical procedures and surgeries, and so forth, but also from glucose-sensing lenses, digital fundoscopes, smartphone visual-acuity tracking, automated refractive error measurements, non-invasive intraocular pressure detection. Head-related data 132 may similarly be obtained by physical examination, but also by seizure records, autonomic nervous activity detection, head-impact sensors, non-invasive intracranial pressure detection, and voice or respiratory stress recognition. Cognition data may be collected through online tests, gamified evaluations measuring mental or physical responses, or through the continuous or episodic tracking of keyboard stroke pressure variation, timing, and other patterns during any typing activity.

Much data 134 relating to body organs and organ systems may be acquired differently based upon the particular physiological structure, including continuous blood pressure tracking for the heart and vascular system, handheld or wearable electrocardiography devices, heart rhythm detection, cardiac output detection, stroke volume measurement, and thoracic impedance measurement. Information on the lungs may be detected, for example, by home spirometry, pulse oximetry, inhaler use, breath-based diagnostics, breathing sounds, and environmental exposure. Regarding the blood, data may be obtained from continuous glucose monitoring, transdermal detection, genomics-based pathogen detection, and blood tests. Skin-related data may be obtained by monitoring temperature, lesions, pressures (e.g., for wound care), sweat chemistry, and cutaneous blood flow. Bladder and urine information may be had from comprehensive urinalysis, sexually transmitted disease tests, and for infants, diaper-based sensors. Moreover, gastrointestinal data may be obtained by endoscopic imaging, esophageal pH monitoring, fecal blood and bilirubin tests, gut electrical activity, and so forth. Other systems, including the skeletal system, the endocrine system, and so forth may be related to other acquisition technologies and methodologies, including many types of medical imaging.

In all cases it is anticipated that additional, refined, and new measuring methods, techniques, and devices will be developed over time that were not either available or practical at the time of the present disclosure. The methodologies and techniques outlined here may nevertheless be adapted to such evolving technologies.

In general, some of these will clearly entail the help of providers, including medical professionals, laboratories, and the like. Others may be based upon direct input by the members (e.g., via the system interfaces, questionnaires, surveys, etc.). Still further, and increasingly, data may be obtained continuously, periodically, or episodically by personal and/or wearable devices, as indicated by reference 136. Such data may include, for example, pulse, blood pressure, temperature, activity, hydration, sleep stages, seizure detection, respiration, oxygen saturation, blood chemistry, ECG, cardiac output, stroke volume, stress, and so forth. Similarly, where available (and permitted by the member), location, movement, interests, treatment compliance, and similar data may be collected from online activities, cellular and mobile device records, and so forth.

FIG. 6B illustrates an example data originating workflow, such as for medical-related data. In many instances, this workflow 138 will begin with an individual 12 visiting a medical provider or institution 110. Based upon the visit and the activities, tests or treatments performed, a record 140 is produced (or typically many such records). These may be made available to the individual (patient), who will then be or become a contributing member. The record is digitized as block 142, either by the provider or upon submission to the system, and one or more structured data/files are produced. These are then stored as indicated by reference 146. As indicated by the arrows returning to the left in the figure, at any of these stages the member or system may loop back to obtain additional data, augment the data, contribute missing data, correct incorrect data or the like. The arrows also indicate that many such loops may be made over the course of the lifetime of the member, and all such data may be collected and processed to enhance the value provided to the member, and its use in the service of the particular member and the community.

FIG. 6C illustrates another example data originating workflow, such as for omic data. In this workflow 148, a sample from any subject of interest may be obtained that may comprise omic material. These may include, for example, the member 12, but also any environment 150 to which they are exposed, any pets or other species 152, or more generally, any relevant source of omic material (e.g., saliva, gut, feces, blood, hair, organ and tissue samples, specimen swabs, etc.). the sample 154 is then processed, typically by a genomic laboratory as indicated by block 156 to produce one or more files containing extended sequences of reads, lists of genomic variants, identified pathogens with antibiotic resistant properties, microbiota presence and abundance, or any other method of conveying detailed or summary information relating to the omic tests conducted. In practice, processed data or summarized data may be provided rather than raw data, and this may be in the form of tag data, text files, or written reports. This data may be contributed, and processed, as indicated at block 158, then stored at block 160. Here again, at any stage of the data acquisition or processing loops back may be useful to complete or correct data, or the process may be repeated one or many times (for the same or tissues) over time.

Figure 7:
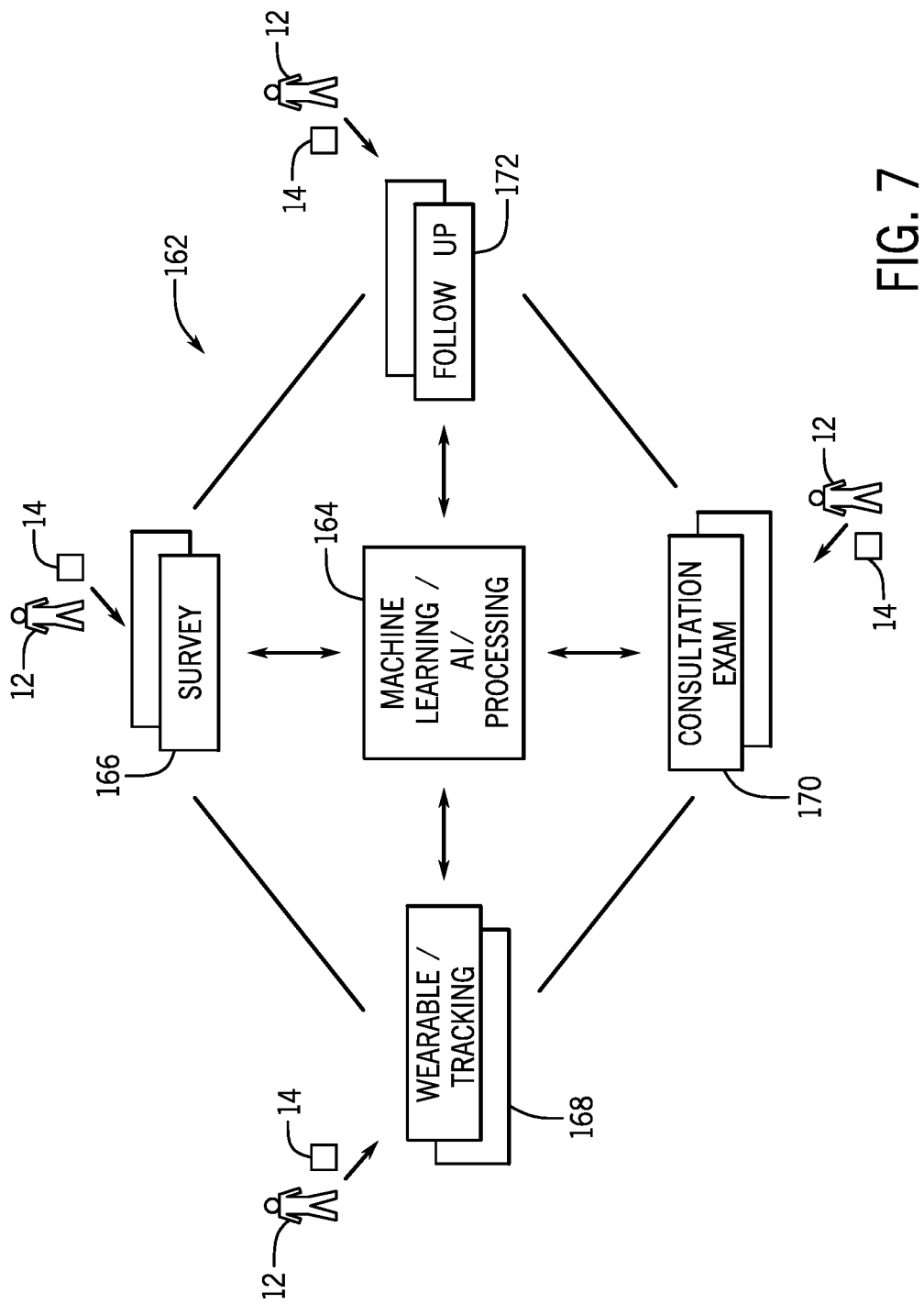
FIG. 7 is a diagrammatical representation of an example interplay between certain data originating and acquisition approaches, and a processing and analysis system that may be maintained and operated by an administrative entity.

FIG. 7 is a diagrammatical representation of an example interplay between certain data originating and acquisition approaches, and a processing and analysis system that may be maintained and operated by an administrative entity. This figure is intended to depict that the system and methodology may be very interactive and interdependent, with data being contributed, received, analyzed, corrected, completed, and used in many different ways, with communications back to the members. In fact, it is anticipated that the ways in which the data is analyzed and used will evolve over time, such as when new conditions are recognized, new data is available, new data types and acquisition techniques are developed, new diagnoses are made, new cohorts are determined, new symptoms develop, and so forth.

In the illustration, the processing 162 may be thought of as centered around the processing system 164, which itself includes the analysis engine. This analysis engine will generally comprise computer code and algorithms operating on local, internet, or cloud based hardware, that may itself have one or more "modules" and that may be progressively developed, refined, and expanded over time. It may be specifically adapted to handle different file types, data types, formats, and so forth. It may also be specifically adapted to identify specific types of gaps and errors in data, to attempt to fill the gaps or correct the errors based on other data of the same type, other data of different types, other data of other members, other data from the same member provided at different types, and so forth. Some gaps and errors may be quite simple (e.g., a mismatch between a zip code and a city), while others may be less intuitive (e.g., the name of a diagnosing physician). Some errors may entail a simple misspelling, while others may require clarification by the member, or more detailed analysis of past records and data for auto-correction.

Such exercises and analysis may be performed at any desired stage of operation of the system. In many cases, initial analysis, completion and correction (with or without communication to the member) may be performed upon or soon after submission of the data to the system. In other cases, analysis may follow submission of additional data of the same or a different type by the same member. Still further, the analysis of one member's data may follow from submission of data from others that may correspond in some way to the first member's data (e.g., relating to a common condition, situation, possible diagnosis, possible health activity, environmental exposure, possible legal claim, etc.).

As shown in the figure, survey data 166 may be provided, and in many cases the first data provided by a member may comprise such data (e.g., geographic information from a home address, simple question/response data). The arrow back and forth to the processing circuitry (and analysis engine) is intended to indicate that the system may request additional data, corrections of the data, completion of the data, verifications of proposed corrections and completions, and so forth, which in some cases may be done during a single data-submission session. Also illustrated is wearable/tracking data 168, which may include any of the technologies and methodologies discussed above. Here again, the correction and completion process may be interactive based upon analysis of the submitted data. Consultation, exam, and similar data 170 may be similarly submitted, and analyzed for completeness and accuracy. Finally, follow-up data 172 may be submitted. Such data may include many different types, including survey data soliciting feedback on whether treatment plans are followed, results of treatment, response of a physical condition to treatment, and so forth. But it should be noted that none of these inputs or data types is limited to occurrence of a disease or condition, but much more generally, they may simply relate to the health and wellbeing of the member.

The figure also represents that over time, and based on various initiators, the system, based upon analysis of contributed data of the member or other members, may interactively solicit completion or correction of contributed data, such as by recommending additional exams, tests, treatments, or simply the updating or supply of other data that may be of use on improving the life and wellbeing of the members.

Figure 8:
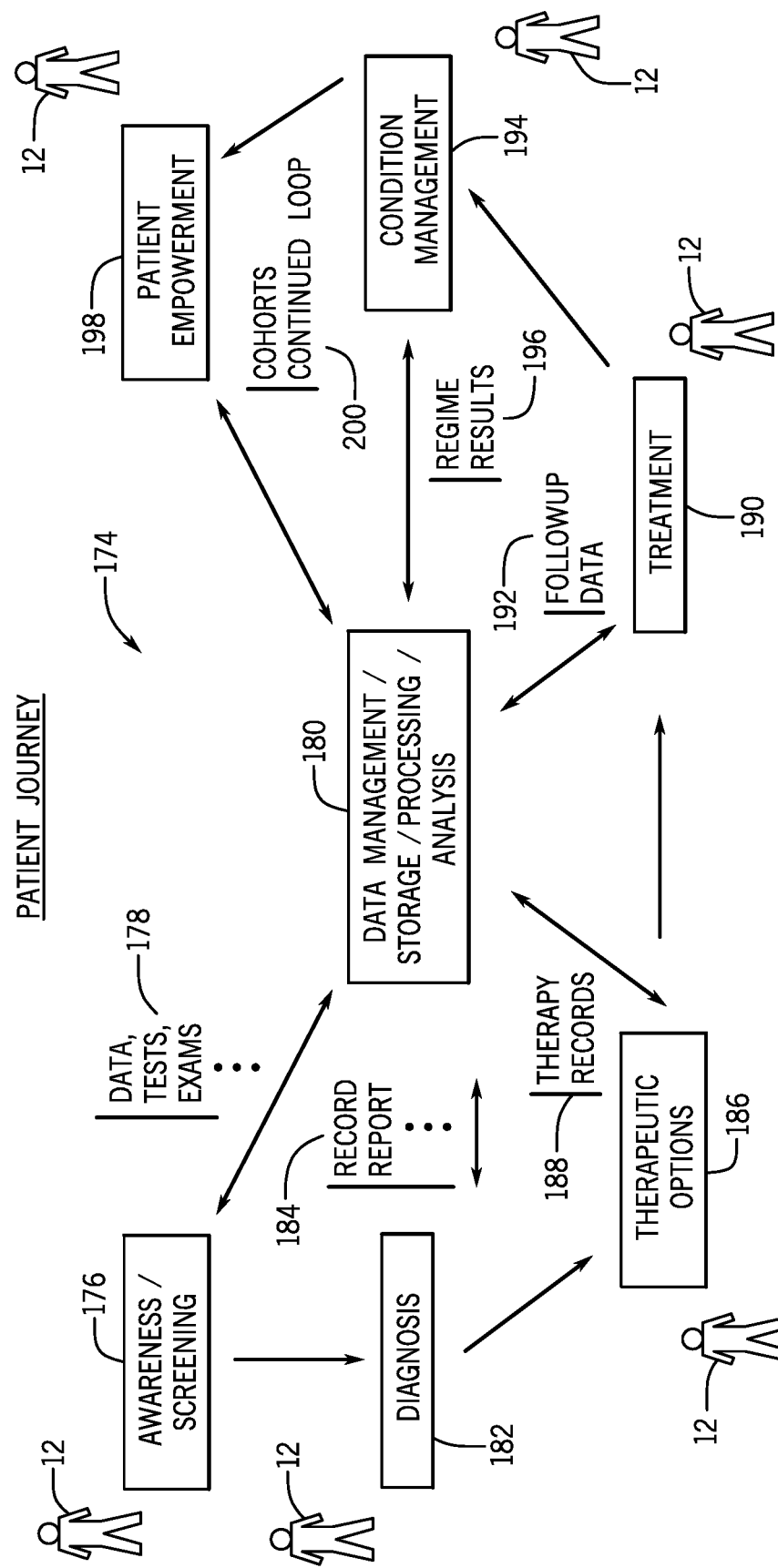
FIG. 8 represents an example manner in which such data originating and acquisition approaches may come into play in a "patient journey" addressing a member physical condition.

FIG. 8 represents an example manner in which such data originating, acquisition, analysis, completion and correction approaches may come into play in a "patient journey" addressing a member physical condition. The term "patient" here should not imply that the member has or will have any particular disease or medical problem, but simply that the process relates in some way to health. In some cases, the "patient journey" will relate to a chronic, acute, or progressive disease or treatable condition, while in other cases it may imply some portion or aspect of the member's life (e.g., normal care stages including prenatal, following birth, vaccinations, standard check-up recommendations of a healthcare system, eye care, regular checkups, regular monitoring, diet management, exercise regime, etc.).

As shown in the figure, the patient journey will in many cases, begin with awareness or screening (or some sort of exam, personal realization, or interaction with a medical or other provider), as indicated at block 176. Such events may include, for example, the development of a condition, symptoms, or the like. But they may also include "normal" life events, such as a birth, initiation of a personal program (e.g., a diet, a workout program, vaccinations, beginning of school, a physical move to a new location, initiation of a self-interested program to acquire omic data, desire to start a family, etc.). Such events may create various data 178, some of which can be provided via online tools, questionnaires, surveys, and the like. Other data may comprise medical tests, exam records, wearable device data, and so forth. Any or all such data, whether initially structured or unstructured may be submitted to the system (managed by the administrative entity) for management, storage, processing and analysis (including aggregation, automated and human-assisted correction and completion, etc.) by the techniques disclosed.

At some point, a diagnosis 182 may be made of some condition, disease, or health or lifestyle concern. Such diagnoses may be made in any suitable manner, such as by conventional medical professionals following visits, but also via remote medicine (e.g. telemedicine), online methods, and certain artificial intelligence and machine learning technologies. In many cases, the member will seek assistance of health or medical professionals, resulting in additional records, data, images, and so forth, as indicated at 184. In some cases, these may be based upon recommendations by the system, as discussed below. This data may then be submitted and processed as well, and analysis may allow for completion and correction.

Later, therapeutic options 186 may be explored or made available to the member. These may address specific diagnosed diseases or conditions. But more generally, "therapeutic" should be read to include steps or activities more generally. By way of example, a pregnant member may consider changes to diet, physical activity, and work schedules. A newborn may benefit from certain types of monitoring, developmental tracking, diet, and so forth. At later stages of life, the member may consider a wide range of lifestyle and other options to address any particular personal concerns. This data 188 may be submitted to the system, and automated or assisted completion and correction may be performed based upon analysis.

Stage 190 represents treatment of a condition or concern. This may involve an actual disease, such as via surgery, prescription drugs, or any other procedure. More generally, it may entail any steps or activities actually taken by the member with or without outside assistance. Data 192 relating to the actual regime adopted may be submitted, analyze, completed and corrected as disclosed. Such information may be extremely useful for determining how the activities address any condition or concern which caused the member to consider them, particularly when considered in connection with data on condition management, as indicated by stage 194. Together, such data may indicate whether treatments are actually followed, whether recommended medication regimes, diets, lifestyle changes, and the like are followed. Condition management data 196 may often include survey data, but may also include medical follow-up reports, lab test results, wearable device data, and so forth. Additionally, data will include information on patient related outcomes and the patient related experience from the treatment, as well as longitudinal data collected months and possibly years after the initial diagnosis and treatment.

In the illustration, the patient journey is completed with patient empowerment 198. The ultimate goal of such activities (and data collection and analysis) is wellbeing of the individual. But this may include benefitting from the journeys of others, and allowing others to benefit from the member's experiences. In the illustration, this stage may produce very interesting data, such as improved determination of cohorts who may share similar experiences. Moreover, it may allow the individual to "loop" back in various ways for the same or a different health consideration. For example, based upon the benefits of interaction with the community and the system, the member may consider closer cooperation with the data contribution process.

The present techniques, platform, and processes offer many unique benefits both to the members and to the community at large based upon interaction during the patient journey. First, it is contemplated that the actual share or value attributed to each member will be increased by the contribution of more and better data. It should be kept in mind that this may entail one or many cycles through the same or different patient journeys for each member, with the same or different initiators and the same or different steps. The analysis of the member-specific contributed data, the aggregated data, and analysis of both together may allow the system to determine and recommend data acquisition, completion and correction based upon similar journeys by other members. Many refinements may be realized as a result of the analysis and data enhancement, including refinement of aggregated data; refinement of recommendations due at least in part to the data reflecting similar concerns, activities and outcomes of others; refinement of efficiency of the journey and steps taken (e.g., by recognizing through data analysis what steps are more or less effective for comparable members with comparable concerns); refinement of screening and prevention (e.g., by the ability to recognize in the member-specific contributed data and the aggregated data potential risks of conditions); identification of previously unrecognized conditions (e.g., new diagnoses recognized by the medical community and determinable by the contributed data); and recognitions of personalized medicine correlations (e.g., based upon deep understanding of the makeup, lifestyle, demographics, etc. of the member, what approaches are most effective based upon the experiences of others).

Figure 9:
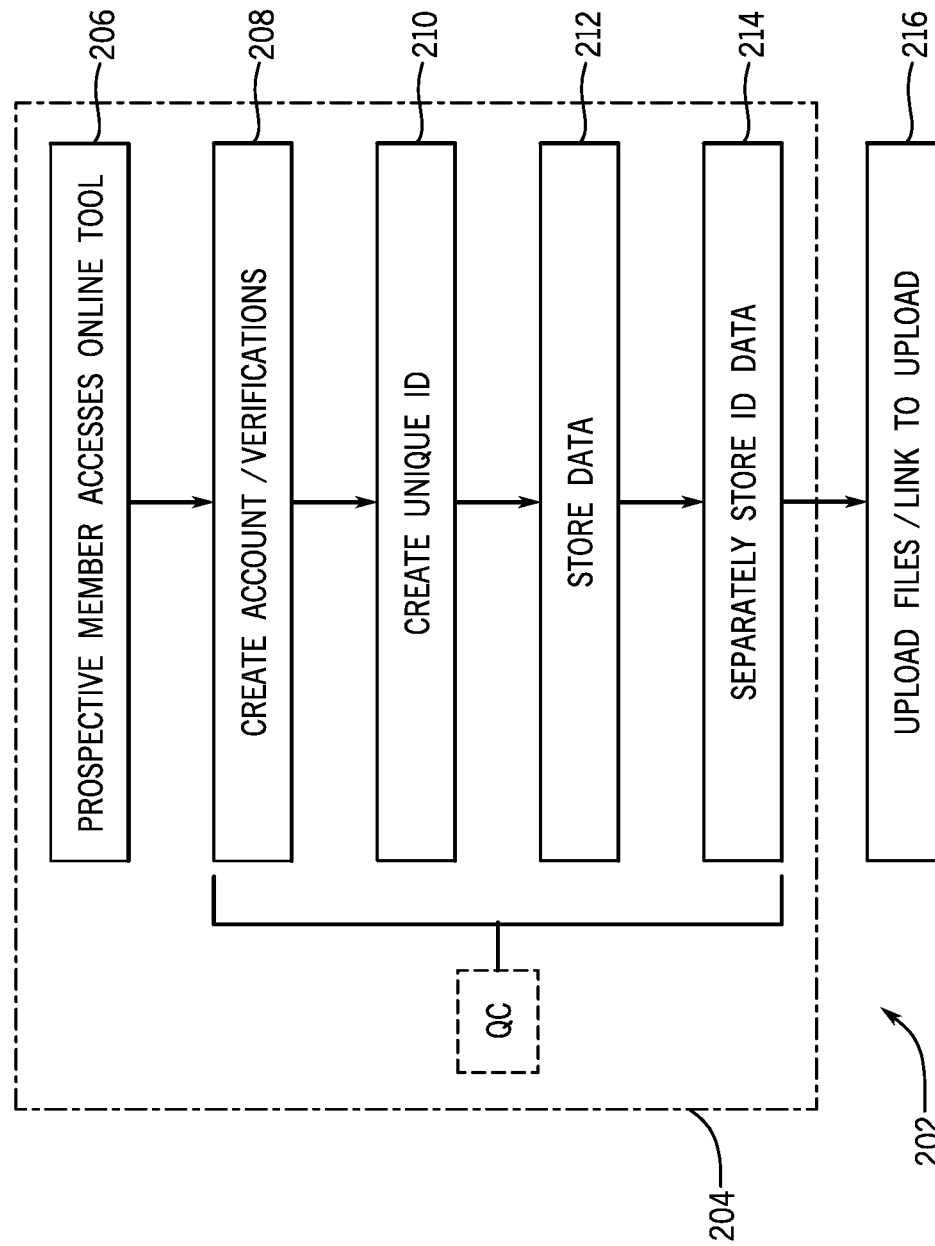
FIG. 9 is a flow chart illustrating an example account initiation and member interaction process.

FIG. 9 illustrates certain example operations 202 that may be considered in processing via the components of the foregoing figures. The process of account creation, indicated generally by reference 204 may begin with a prospective member accessing an online tool as noted at operation 206. This online tool may take the form of a screen or screens that permit input of data and provide directions and information to the perspective member. At operation 208, then, the prospective member creates an account and this account may be verified, such as by verifying an email contact for the member. At operation 210, then, a unique member ID is created. Importantly, this member ID may be used for all member interactions with the system, and is a part of the basis for separating individual or personal data from the data uploaded for aggregation. That is, respecting member anonymity or confidentiality, the unique ID allows for many types of member interaction with the system while maintaining separation between the aggregated data or files and the personal identification of the member. The member idea may be encrypted locally on the member computer using member login information, such that it is not directly linked to the member's account until it is unencrypted.

At operation 212, then, any information provided by the new member is stored, and at operation 214 identifying information is separately stored. It may be noted that through all of these operations, and based upon the protocols set forth in the smart contract, quality control and other required operations or milestones may be performed as indicated by block 216. For example, when data is uploaded the smart contract may call for a quality control operation on the data and a response may be defined, such as receiving a quality control metric, as well as an action may be taken, such as to compare the metric to a pass/fail hurdle, to make a pass or fail decision, and so forth. Responses may also be defined at such steps, such as indicating to the user whether data is acceptable or not, whether data or files pass or fail, and, for example, if the response is a "pass" the data may be entered into the database, shares in the database may be allocated, entries may be made to a ledger, and so forth as described below. Similarly, in the case of a "fail", actions may include placing data into a failed data queue, informing the user, making a leger entry, and so forth.

It is also contemplated that the member may have direct access to certain data and files, and in such cases, may upload the data or files directly. In other cases, the member may instead provide links to data and files that can be the basis for access by the processing systems of the administrative entity. In yet other cases the members may fill out a survey and the data would be extracted from the answers directly or after quality control testing and other processing.

Figure 10:
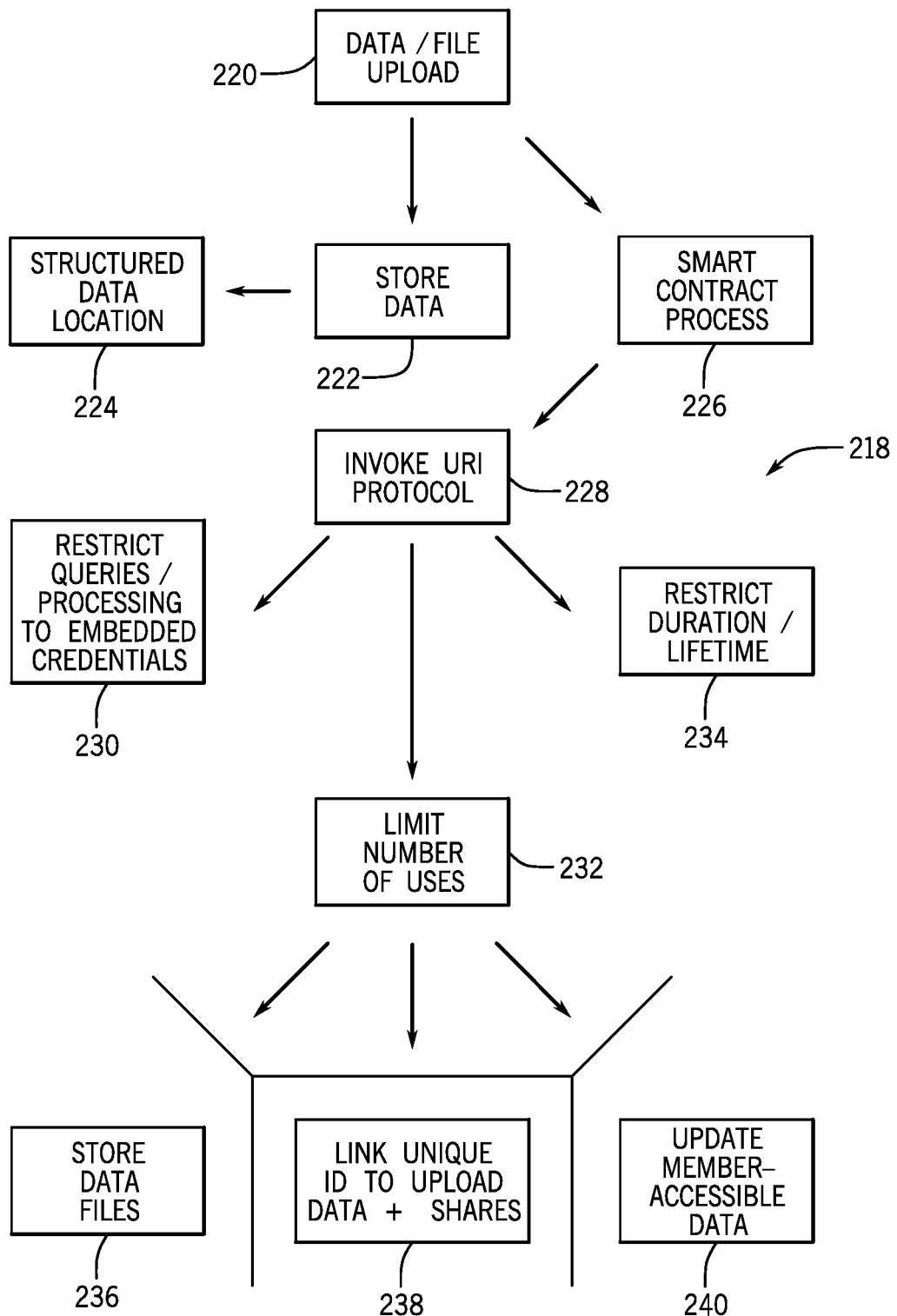
FIG. 10 is a diagrammatical representation of an example process for transparent confidentiality in processing member data.

FIG. 10 illustrates exemplary logic for providing transparent confidentiality in processing of member data and files. As noted throughout the present disclosure, an important aspect of the system is the ability to reliably trace interactions with the system, and between members and the system, as well as third-parties in the system. Such interactions should not only be transparent and reliably traceable, but should also respect the confidentiality of the participants, and particularly of the community members. Various processed may be envisaged and implemented to provide both the desired tracing and transparency needed for reliability, as well as member confidentiality. In general, this is done by separation of member identifying data from uploaded data in files. The latter becomes de-identified data which cannot ordinarily be associated with the identity of the contributing member. Nevertheless, the system allows for the account to be created, augmented, and for value (e.g., remuneration) to be passed along to the particular members based upon third-party utilization of the database or databases.

In the implementation illustrated in FIG. 10, this process 218 again begins with the uploading of data or files as indicated by reference 220. When the data is uploaded it is stored as indicated by reference 222 and as discussed above. The data may typically be stored at a structured data location as indicated by 224. Moreover, this process again begins a protocol in accordance with smart contract processing as indicated by reference 226. Though not separately illustrated in FIG. 10, it should be borne in mind that this smart contract processing may include individual stages or toll gates that are passed, and each may be associated with actions, responses, notifications, and so forth, all of which are recorded in one or more ledgers.

At block 228, the processing invokes a universal resource identifier protocol (URI). Such protocols may be crafted to provide restricted processing of the data stored at location 230. For example, in a presently contemplated embodiment, the URI protocol will require credentials which may be embedded into queries made by the administrative entity. Accordingly, such queries may be the basis for the processing performed by the administrative entity, and because it is exceedingly unlikely that such credentials could be reproduced by other entities, the URI protocol ensures that only such queries will meet the requirements for response. Moreover, in the presently contemplated embodiment illustrated, a limited number of uses may be made of the data in accordance with the URI protocol as indicated by reference 232. In this contemplated embodiment, a single use is permitted. Further, in accordance with this embodiment, a restriction on the duration or lifetime of the availability of the data or URI is made as indicated by reference 234. Once this time expires, the queries are no longer permitted and the process must move to an earlier stage, possibly including re-uploading of the data.

The figure also illustrates the separation of subsequent operations. For example, based upon processing, and as discussed above, data and files are stored as indicated by reference 236. In a separated way, however, user accessible data is updated as indicated by reference 240. That is, the user account information, value or shares attributed to the user, and so forth may be accessible to the user, while the same information is not accessible to the administrative entity, owing to the separation of the data and files stored at block 236 from the user information accessible at block 240. As indicated at 238, however, the user identity and uploaded data, files, and share information may be linked so that attribution may be made, and remuneration passed along to the members based upon the uploaded data and files, and their utilization by third-parties.

Figure 11:
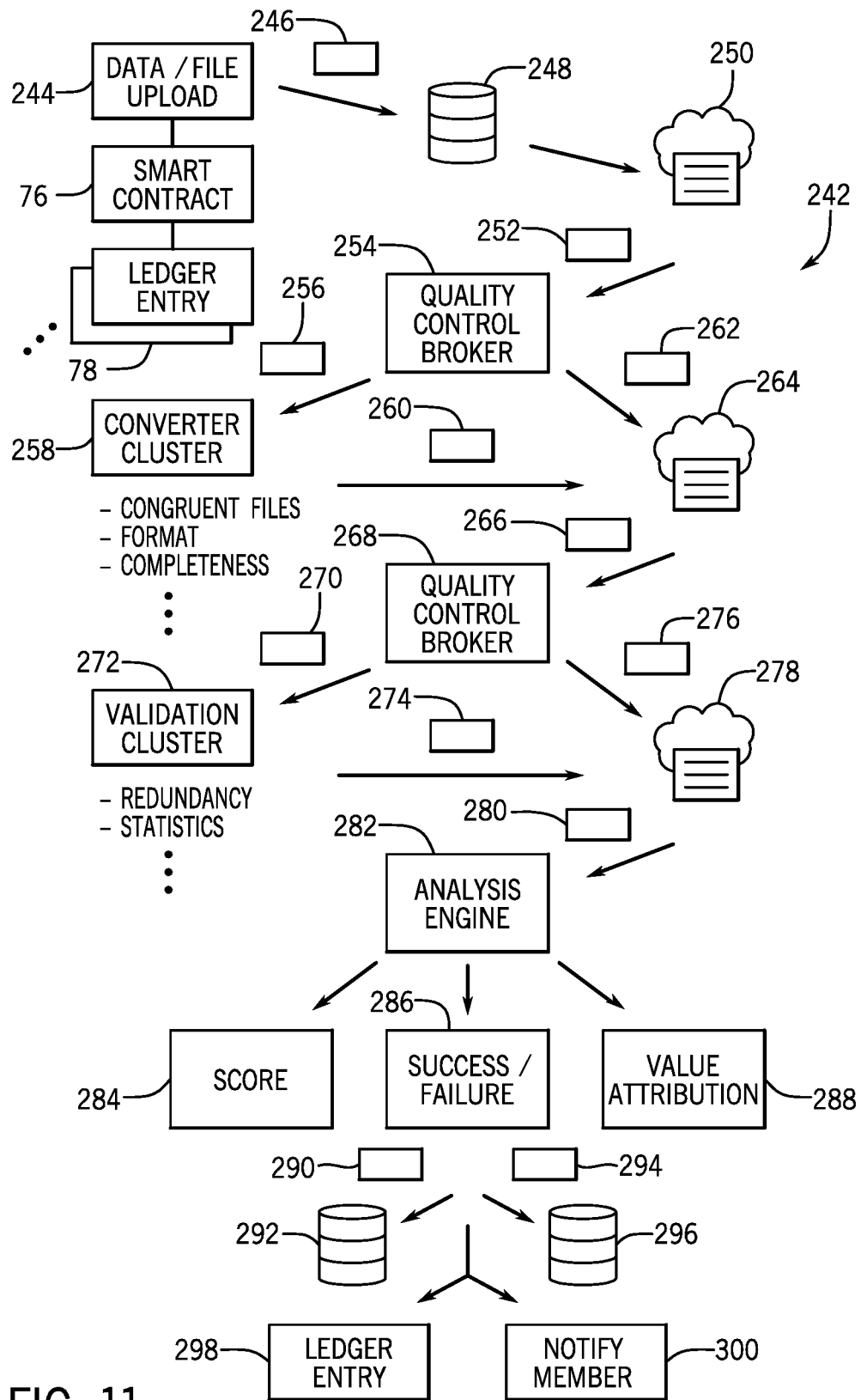
FIG. 11 is a diagrammatical representation of an example process for member data processing and quality control.

FIG. 11 illustrates example processes 242 presently contemplated for uploading, receiving and processing member data files. The processes may begin with the uploading of data or files as indicated at block 244. As noted above, all search processes may be performed in accordance with protocols established by one or more algorithms or smart contracts (or "smart code" or other suitable immutable and traceable protocol) as indicated at 76 in FIG. 11. Each stage executed may include initiating actions, receiving responses, and taking actions based upon received responses. For each of these steps or stages in execution of the smart contract, and based upon the interactions between the system and the member, ledger entries are made as indicated at reference 78 to maintain a reliable record of the interactions. Though not separately illustrated in FIG. 11, such smart contract stages and ledger entries are made or may be made at all of the various steps of processing.

The uploading process transfers data or a file 246 to one or more temporary storage systems 248. Temporary content storage, as indicated more generally by reference 250 may store unprocessed or partially processed data or files waiting in a queue for other actions, such as quality control. Individual files 252 are then transferred by a quality control broker 254 for one or more types of quality control. In certain presently contemplated embodiments, structured data or files may be converted or processed to make them more structured, understandable, comparable, searchable, or to facilitate extraction of data for aggregation. Such files, as indicated by reference 256, may be transferred to a converter cluster 258. Genomic data files, as well as any other contributed data or files, for example, may be most useful when placed into a structured and standard format or when stored based on comparison to a reference file. Converter cluster 258 may provide processing for creating congruent files, verifying that the files relate to a particular population, species, individual, and so forth, for formatting the files and contents of the files and so forth. Where such processing or conversion is not desired or required, the files may be passed to a quality control process content storage 264 as indicated by reference 262, or the converted or processed files may be similarly placed in the quality control process content storage as indicated by reference 260 in the figure.

Files waiting in a queue in the quality control process content storage may be individually transferred, then, as indicated at 266 by a quality control broker 268 to perform validation on the files. The files sent for validation, indicated at reference 270 are considered by a validation cluster 272. Validation of data or content of such files may be performed based upon the type of data in the file, expected aspects of the data, standard data to which the processed data may compared, and so forth. For example, the validation cluster may check for redundancy or near redundancy (e.g., a member has uploaded the same data more than once, or copied a file and has made one or few changes, commonality of variants (e.g., the member has uploaded inconsistent files), verifications versus reference data (e.g., genomic data compared to human or other species reference genomic data), statistical analysis of the data, and so forth. The validation cluster may produce a validation or analysis report. Thereafter, the validated or processed files 274 may be transferred to a validated data storage 278. If such validation is not desired or required, the files may be forwarded to the storage 278 bypassing the validation cluster, as indicated at reference 276.

Individual files may then be extracted from the validated data storage as indicated by reference 280 to a data analysis engine 282. In particular, various types of quality, credibility, reliability, completeness and aspects of the data may be measured, and scores may be attributed that may be used for various purposes, including, where desired, attribution of shares or value. Other types of analysis, discussed in the present disclosure, may include, for example, determination of useful follow-up communications with members, recommendations for further data acquisition, tests, and so forth, determination of possible membership in cohorts based on the data, and many other processes.

A credibility or data quality score or report may be generated at operation 284. Based upon such scores, certain members may be designated as "trusted" or reliable members, and later processing of contributions by such members may be altered, such as by alteration of certain quality control applied to the data or files, or value attributed to the data or files based upon the quality and/or reliability of the underlying data. At this or a later stage, the system may analyze data of the same or a different type, or data received at different times, and attempt to complete or correct the data, as described below. Other operations, such as creation of a customized template or survey may be performed, such as to solicit the contributing members to complete or correct contributed data that appears to be incomplete or inaccurate. When the data is completed or its accuracy (or more generally, its quality) is improved, such improvements may be reflected in increases or changes in the value attributed to the contributing members. The score may be saved and be used later as part of a statistical analysis evaluating the overall quality of all the data provided by a user or the statistical confidence of conclusions in a study across multiple users. At operation 286, the analysis engine may also determine that the processing of the data is successful or that a failure has occurred, requiring either sequestration of the data, partial acceptance of the data and so forth. At operation 288, then, value, ownership increment, profit distribution, or shares may be attributed to the member based upon the data. Any suitable formula for attributing value may be applied at this stage, and different formulas may be developed as different types of data and data of interest are determined and provided by members.

Finally, as indicated at references 290, 292, 294 and 296, the data and files are stored. In presently contemplated embodiments, these are stored in separate storage spaces, with genetic files being stored in a first storage space 292 and medical and similar data and files being stored in a storage space 296. Of course, each of these storage spaces may comprise one or many different physical storage media and locations. As noted above for all of the steps and based upon the smart contract protocol implemented, ledger entries are made as indicated at reference 298, and notice is provided to the members of the processing and value attribution as indicated by reference 296.

As noted above, various approaches and formulas may be used for the attribution or allocation of shares or value based upon the data and files provided by members. Exemplary processes for such value or share attribution may begin with evaluation of the type of data provided by the member, such as personal data, medical data, health records, history data, omic data, or any other type of data. The system may then perform analysis and quality control on the data as noted. Many other factors may be considered that can be incorporated into the evaluation, particularly completeness, consistency, and so forth. Such completeness and consistency may be analyzed within and between data and files contributed by the same member at a single time or between data contributed at different types. Similarly, completeness and accuracy may be determined between data types (e.g., to ensure that data of one type is consistent with data of another type). Data may also be analyzed versus similar data (e.g., data of the same or similar type) contributed by other members, or even aggregated data for many members. Further, where standard data (e.g., reference omic data, reference disease state data, etc.) is available comparisons may be made with such references. Complex computation of shares or value for individual members and for individual data may be made by the system. In general, the sum of all value attributed to the individual member can be applied regardless of the number of times the data is added, altered, supplemented, removed, and so forth. Based upon factors such as the completeness, accuracy, consistency, quality, reliability, veracity, and so forth, then, the shares calculations may be applied. The calculation could be a simple score used to accept or reject contributed data or the score could be used to weight the data value and subsequently the share allocation. As always in these processes, where smart contracts are utilized, a ledger entry may be made and the member may be notified.

Figure 12:
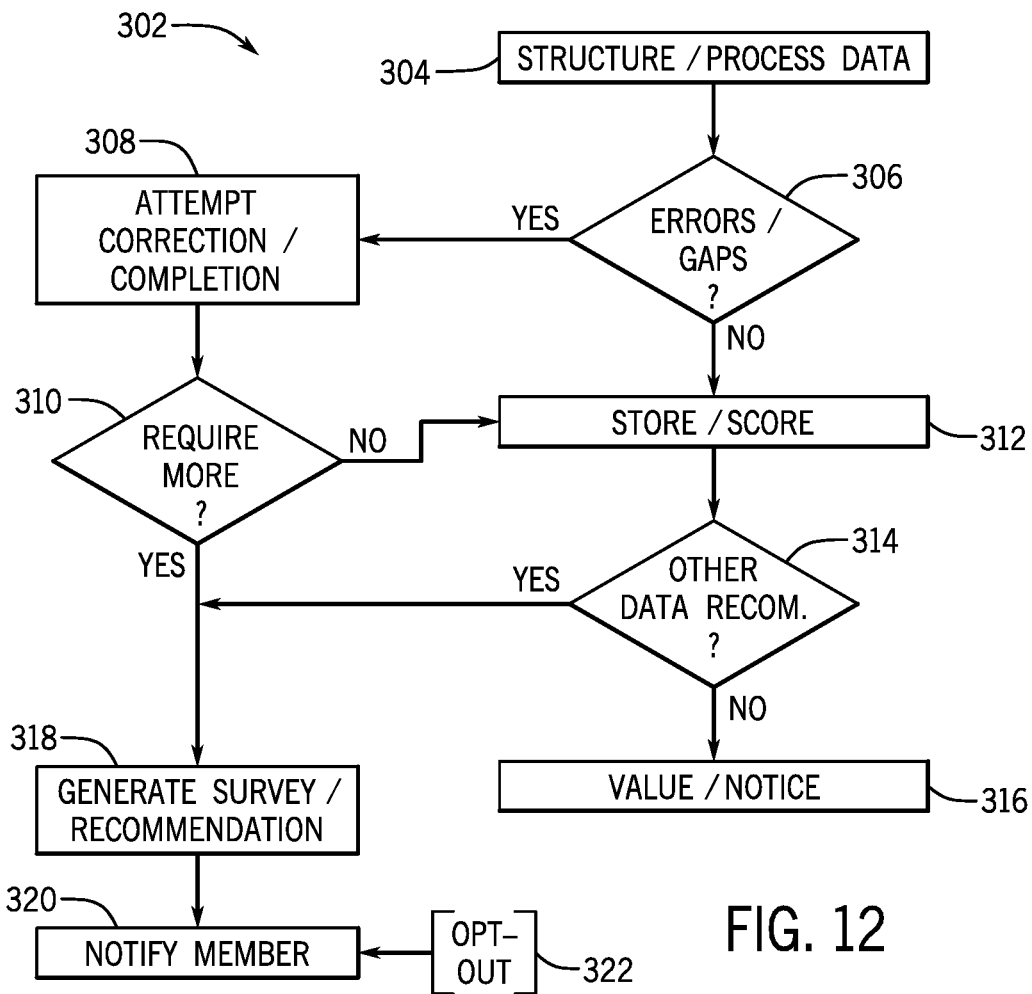
FIG. 12 is a flow chart illustrating an example data gap or error identification and correction process.

FIG. 12 is a flow chart illustrating an example data gap or error identification and correction process 302. As noted above, upon receipt of member-specific contributed data, the analysis engine determine whether the data is incomplete or incorrect, and attempt to complete and/or correct the data. This may be done on the data in either a structured or unstructured form, although in some cases the data may be converted to a structured form that is more easily analyzed prior to analysis for incompleteness and errors. In the illustrated embodiment of FIG. 12, the data is structured and processed at operation 304. One or more analysis routines or programs may then be invoked and executed, and based upon such factors as anticipated fields, desired fields, textual and/or contextual analysis, the system determines whether any gaps, incompletions, or errors are present in the data at operation 306. If any are detected, the system may attempt to provide the missing information or to correct the errors, as indicated at 308. Simple errors of spelling, dates, names, addresses, and so forth may be provided by reference data, or by comparison of the contributed data to other contributed data from the member, or from data of other contributing members (e.g., in a similar location, with the same or similar providers, etc.). Artificial intelligence and machine learning techniques may also be employed, such as to infer the likely missing or correct data from other data for the same or other members. It is contemplated that over time, such techniques will learn patterns and typical gaps and errors, both for the same and other members.

If such attempts do not provide all of the desired data, the system may communicate with the contributing member to solicit additional or correct data as indicated at operation 310. It is contemplated that such communications will be made in a "de-identified" manner, wherein the identity of the member is not available to the administrative entity. At this point, or if no gaps or errors were identified, the data may be stored, as indicated at operation 312. Even in such cases, the analysis engine may determine that, at least partially based on the contributed data, other data recommendations may be desirable. Such determinations may be based, for example, on analysis of conditions or health concerns that may be detectable by analysis of the contributed data, including analysis in combination with other data types from the same member, or earlier-contributed data of the member. Moreover, such recommendations may be based upon analysis of a patient journey of the type described above. They may also be based upon aggregated data of other members, particularly members with correlations to the contributing member. Further, such recommendations could be based upon newly identified conditions, diagnoses, medical innovations, development of new tests and screening techniques, and so forth. It is contemplated that the routines executed by the analysis engine will evolve and develop to accommodate such new comparisons and recommendations. If no further recommendation is identified, the value attributable for the data may be noted and notice provided to the member at operation 316.

It should be noted that, though not separately indicated in FIG. 12, it is contemplated that each operation will result in one or more entries into an immutable ledger or tamper-evident ledger in accordance with a smart contract or smart code protocol. Moreover, as noted above, the analysis and processing may be accompanied by determination of a data quality score or similar evaluation, which may serve at least partially as the basis for the value determination. Many different approaches may be made so such scoring, including higher scores for more complete or accurate data, higher or lower scores determined by comparison of the contributed data to similar data from other members (e.g., as gauged by the aggregated data), and so forth.

If more data is desired at operation 310, or any recommendations are available at operation 314, the communication mentioned above may be created at operation 318, and a de-identified notice sent at operation 320. In general, it is contemplated that such communications may comprise an email, message on an internet login page, or other notification and an automatically populated survey, template, form, document, or other online tool that prompts the members to provide, correct, or confirm the data of interest. It should be noted that, as indicated by reference 322, at this or any other stage in the processing, the contributing members may "opt out" of various operations. This is particularly the case for notifications and requests for additional data, or recommendations. For example, some members may not desire to know of potential conditions or concerns, regardless of the potential for additional shares or attributed value. A fundamental principle of the system is to maintain member confidentiality and to respect their desires with regards to the use and analysis of the contributed data.

Figure 13:
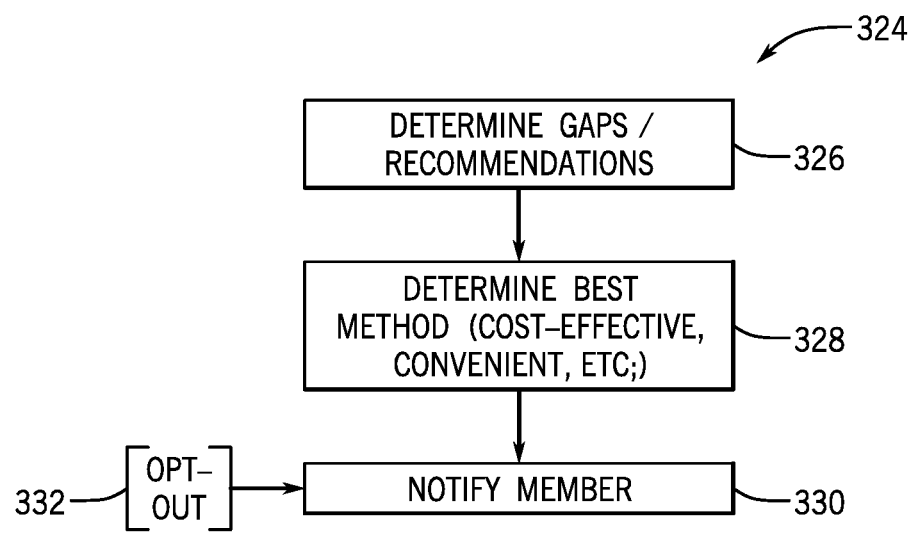
FIG. 13 is a flow chart illustrating an example process for recommending data gap filling, complementing, and completion.

FIG. 13 is a flow chart illustrating an example process for recommending data gap filling, complementing, and completion. As noted, the follow-up communications with the members may entail recommendations for acquisition or communication of more complete or complementary data.

The process 324 for such recommendation may allow for assisting the members in this way. That is, when gaps, errors or recommendations are determined, as indicated at operation 326, the analysis engine may determine the best method for obtaining the data, as indicated at operation 328. Many different types of data may be used in this process. For example, the system may determine providers that the member already uses or has used in the past. It may also consider providers in the members geographic area. Still further, where available, the system may access information on candidate providers, such as ratings, reviews, cost data, insurance plan data, and so forth. Such data may include consideration of results (e.g., data quality) experienced by other members, the form, format and completeness of the data typically available from providers, and so forth. Based upon such considerations, one or more providers, protocols, locations, and so forth may be communicated to the member as indicated at operation 330. Here again, at indicated at 332, the system may allow for opting out of this process or of the notification of operation 330.

Figure 14:
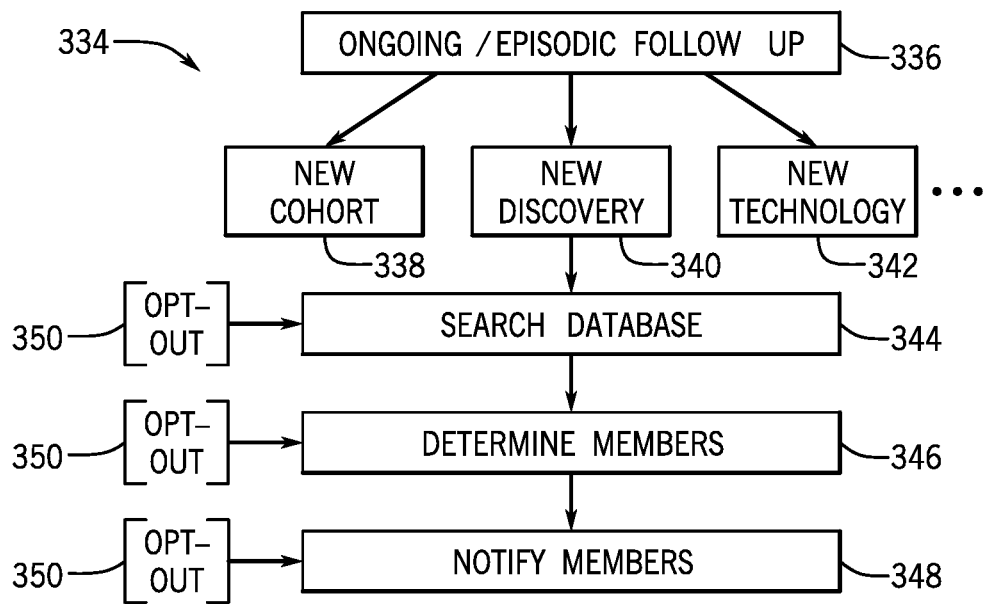
FIG. 14 is a flow chart illustrating an example process for identifying potentially useful new data for members, and recommending follow-up.

FIG. 14 is a flow chart illustrating an example process for identifying potentially useful new data for members, and recommending follow-up. The process 334 may begin with an ongoing (e.g., continuous, periodic) or episodic follow-up initiation as indicated by reference numeral 336. It should be noted that follow-up communications may already be made to solicit or collect the provision of completing or corrected data as discussed above. The illustration of FIG. 14 relates to further or later communications that may be made for other reasons, on a regular or "from time to time" basis.

Any of a wide variety of events may initiate the follow-up communications. In the illustration, for example, follow-up communications may depend upon determination of a new cohort that could include the contributing member, as indicated at 338. Further, when contributed data of the member, aggregated data, and/or contributed data of other members indicates that a new discovery is available, communications may be initiated to members that may benefit from the discovery, as indicated at 340. Such discoveries may comprise, for example, determination of a potential new condition, diagnosis, relation between data and a potential patient journey, and so forth, to mention only a few. Similarly, upon the development of new technologies, as indicated at 342, members may be notified. Such technologies may include, for example, new methodologies for collecting data, new devices available for acquiring data, and so forth. Here again, many other bases may be considered for initiating such communications.

At operation 344, then, the member-specific contributed data and/or the aggregated data is searched to determine members who may benefit from the communications. At operation 346, those members are determined (albeit in a manner that avoids identification of the individuals by the administrative entity). And at operation 348, notifications may be sent to those members, such as via a de-identified email. It should be noted that in all of these operations, the members may opt-out of consideration, as indicated by reference numeral 350.

As noted above, the communications are de-identified so that the individual members are not personally identified to the administrative entity, to researchers, or when applicable, to other members. Moreover, as summarized above, where suggestions or recommendations are made for the acquisition or contribution of additional data, such recommendations may be advantageously refined by identification of "best" locations, providers, and so forth.

The processes outlined in FIGS. 12, 13, and 14 may be used in combination, and in some presently contemplated embodiments, certain patient journeys may be the basis for "templates" that are used to prompt the completion or provision of follow-up member data by automated communications and recommendations. Such templates may be considered pathways or anticipated events in the lives of members, and may be associated with milestones or timelines depending upon the nature and focus on the particular template. It should be noted that at least some templates may be "dynamic", that is, they may be changed over time, such as to update them with the most current information, practices, or approaches in the field so that members may benefit from ongoing changes, developments, technologies, and discoveries.

In an example approach, for example, templates are stored in the system or database for anticipated events or information in a patient health journey. The processing circuitry automatically and without human intervention sends follow-up de-identified communications to specific contributing members to prompt contribution of follow-up or missing member-specific contributed data based upon the template. For example, each template may include anticipated events in a different patient health journey. The templates may be based upon analysis of the aggregated member-specific contributed data indicative of events of other contributing members on the same patient health journey, such as contributed data from members who may have a similar condition or symptoms.

Moreover, the templates and corresponding follow-up communications may be implemented for particular contributing members based upon initiating events that are unique to the particular patient health journey and template. Such initiating events may include, for example, a birth, the occurrence of new symptoms or conditions indicated by the patient-specific contributed data, a diagnosis indicated by the patient-specific contributed data, a treatment plan indicated by the patient-specific contributed data, identification of a physical condition potentially detectable from the aggregated member-specific contributed data, identification of a new treatment of a physical condition detectable from the aggregated member-specific contributed data, or identification of a new examination or test useful in determining a physical condition detectable from the aggregated member-specific contributed data.

The templates may be adapted, changed, or added over time, and may give rise to different standard or member-adapted reports, surveys, and recommendations. For example, the follow-up communications based upon the templates may include a custom report adapted to facilitate a contributing member consulting a medical professional, or recommendations for acquisition of additional data of the respective contributing members. Where the member-specific contributed data comprises health-related data, the recommendations may comprise at least one physical examination or test related to physical condition of the respective contributing members. Here again, the processing circuitry may analyze the member-specific contributed data of each member to determine at least one most convenient and/or cost effective source for the acquisition of additional data, and the recommendations may include an indication of the most convenient and/or cost effective source for each respective recommendation to each respective contributing member.

As with other occurrences of contributed data from members, the processing circuitry may re-evaluates the member-specific value after receipt of follow-up member-specific contributed data from each respective contributing member. In such cases, the follow-up communications may comprise an indication to each contributing member of the re-evaluation of the member-specific value applicable when the respective contributing member contributes the follow-up member-specific contributed data.

As noted above, a particularly powerful use case for the platform, and the member-specific contributed data and aggregated data is the determination of correlations between and among members sharing the same or similar characteristics. Such groupings, referred to in this disclosure as "cohorts" may be determined based upon one or many factors detectable in the contributed and aggregated data, such as a physical condition, a diagnosis, a family situation, a predisposition, a patient journey, and so forth. But many other factors and bases, data types and combinations of data may be considered for determining cohorts, such as any of those discussed above (e.g., demographic data, personal data, geographic data, omic data, employment data, health history, lifestyle, habits, interests, etc.)

Figure 15:
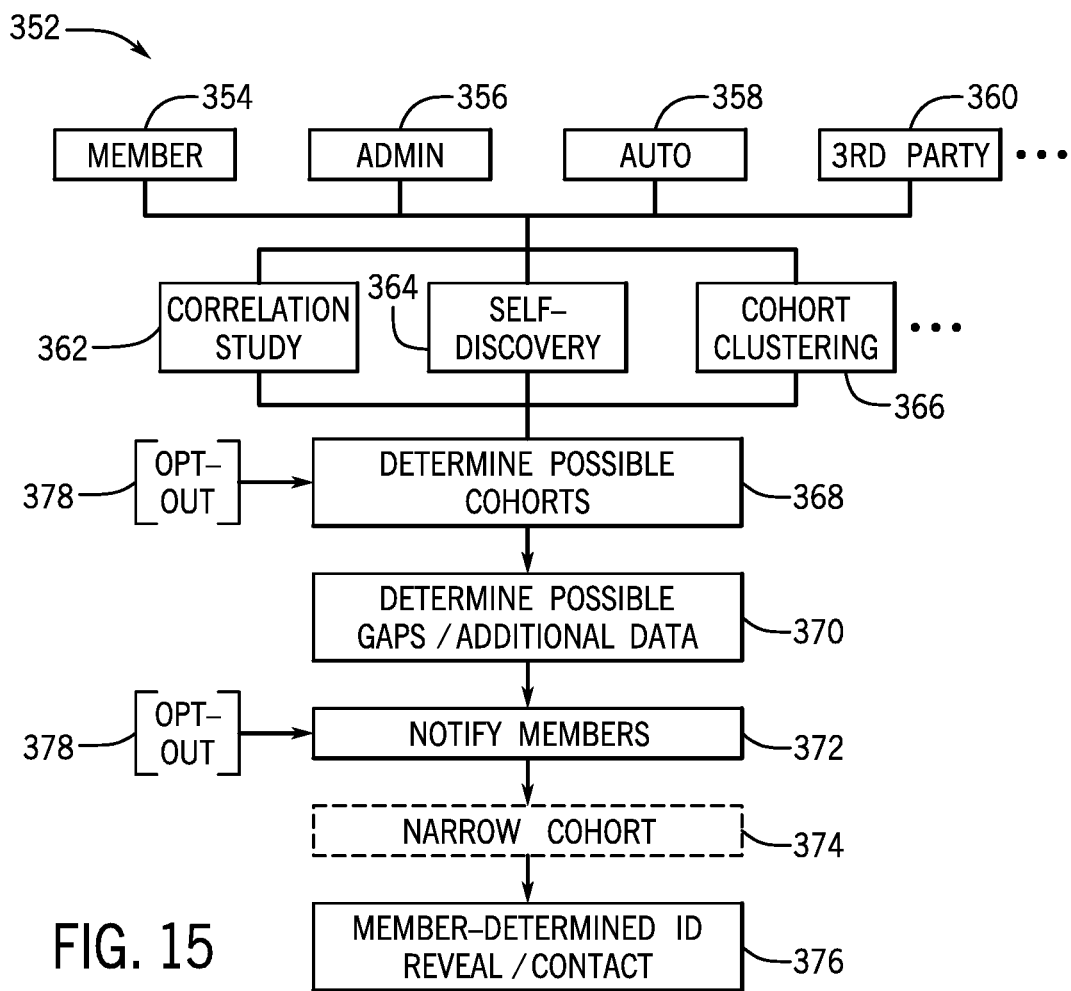
FIG. 15 is a flow chart illustrating an example process for analyzing member data to provide enhanced value by determining cohorts among members for possible data sharing and follow-up.

FIG. 15 is a flow chart illustrating an example process for analyzing member data to provide enhanced value by determining cohorts among members for possible data sharing and follow-up. The cohort process 352 may be initiated by any suitable actor, including by contributing members 354, the administrative entity 356, by automatic operation (e.g., programming) of the system (e.g., processing circuitry and analysis engine) 358, by research by interested third-parties 360 (e.g., health and medical institutions and companies, pharmaceutical firms, etc. contracting with the administrative entity), and so forth. The initiation of cohort identification launch execution of analysis routines that are pre-established or that may be at least partially defined by the initiating entity (e.g., based upon a query or search submitted via an online tool). In the illustration, several such searches are summarized, including a correlation study 362 to determine members who may exhibit some statistical correlation to search criteria, self-discovery 364, which may be considered a more "free-form" analysis for any potentially meaningful correlations, and cohort clustering 366, which may use any of various clustering algorithms to group members on the basis of particular characteristics or combinations of characteristics.

The analysis may ultimately result in a listing of possible members of one or more cohorts. The listing may be qualified, such as by the confidence level or strength of correlations of the member-specific contributed data to the criteria of the cohort. In keeping with the data completion and correction aspects of the present disclosure, in many cases, this confidence level may be greatly enhanced by identifying additional data that could be contributed by candidate members to a cohort, and soliciting the members to consider adding such details, such as by surveys, tests, exams, and analyses. At operation 370, such gaps or desired data may be determined. As before, these determinations may include determination of member-specific recommendations, including, for example, the suggested data, tests, and exams, as well as where and how to go about acquiring the data, having tests and exams performed, the most cost-effective manner of proceeding, and so forth.

At operation 372 de-identified communications may be sent to the candidate members. Based upon responses, then, the cohort may be narrowed (or in some case expanded), as noted at operation 374. This narrowing (or expansion) may be based upon improved statistical correlations or confidence levels resulting from the completion of contributed data by members. Narrowing is valuable due to the fact that historically diseases or conditions have been defined based on the classification of symptoms or analytical tests. Often the molecular basis could not be ascertained. As a results a single disease or condition classified by historic methods may, and often has, multiple different molecular causes. Each individual molecular basis may require an individual treatment to address or resolve the disease or condition. The fact that one disease may have multiple causes at the molecular level can confound attempts to identify correlations between a disease and genomic signatures. Increasing statistical power can be achieved for instance by increasing the depth, breadth, and scale of the study or by narrowing the cohorts in an attempt to reduce the number of different molecular causes in a single cohort.

In some cases the members of cohorts may desire to communicate with one another, or even with the administrative entity or third-parties (e.g., research institutions). This is possible, as indicated by operation 376. In general, and again in keeping with the member confidentiality values of the platform, such communications and revealing of an individual member identification is strictly at the option and control of the particular members. Similarly, it should be noted that at various stages of cohort determination, analysis, and communication, the members may opt out of consideration and notification, as indicated by reference 378 in FIG. 15.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
a server device including a processor and memory that cooperate to, in operation, facilitate interaction with contributing members of an aggregation;
a database maintained by an administrative entity that, in operation, stores and aggregates member-specific contributed data transmitted by contributing members with member-specific contributed data contributed by other contributing members; and
processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;
wherein the stored and aggregated member-specific contributed data is de-identified from the member-specific account data; and
wherein at least part of the member-specific contributed data is transformed from a form received from contributing members to a structured and standard format prior to storage in the database and the aggregation is performed on the structured and standard format member-specific contributed data; and
wherein the processing circuitry periodically analyzes the aggregated member-specific contributed data to determine cohorts of contributing members based upon correlations between the member-specific contributed data for each contributing member; and wherein the processing circuitry permits communications with contributing members of a cohort without revealing identification of respective contributing members to the administrative entity.

2. The system of claim 1, wherein a cohort is determined based upon at least one parameter that is common to all contributing members of the determined cohort.

3. The system of claim 1, wherein a cohort is determined based upon a criterion established by a third party analysis of the aggregated member-specific contributed data.

4. The system of claim 1, wherein the processing circuitry determines the cohorts by episodic analysis of the aggregated member-specific contributed data, or upon contribution of data by a new member, or upon entry of new contributed data by an existing member, or following correcting, updating, or improving a statistical fit.

5. The system of claim 1, wherein the processing circuitry determines the cohorts based upon analysis of the aggregated member-specific contributed data initiated by at least one contributing member.

6. The system of claim 1, wherein the processing circuitry determines the cohorts based upon analysis of the aggregated member-specific contributed data initiated by identification of a physical condition potentially detectable from the aggregated member-specific contributed data.

7. The system of claim 1, wherein the processing circuitry determines the cohorts based upon analysis of the aggregated member-specific contributed data initiated by identification of a new treatment of a physical condition detectable from the aggregated member-specific contributed data.

8. The system of claim 1, wherein the processing circuitry determines the cohorts based upon analysis of the aggregated member-specific contributed data initiated by identification of a new examination, test, or omic pattern useful in determining a physical condition detectable from the aggregated member-specific contributed data.

9. The system of claim 1, wherein the processing circuitry determines the cohorts without identification of the contributing members to the administrative entity.

10. The system of claim 1, wherein the cohorts comprise contributing members sharing a physical or health condition.

11. The system of claim 1, wherein the cohorts comprise contributing members sharing a disease state, condition, or sensitivity.

12. The system of claim 1, wherein the cohorts comprise contributing members sharing a potential legal claim.

13. The system of claim 1, wherein the processing circuitry permits communications between contributing members of a cohort without revealing identification of respective contributing members to the administrative entity.

14. The system of claim 1, wherein the processing circuitry permits communications between contributing members of a cohort without revealing identification of respective contributing members to other contributing members unless such identification is done by the respective contributing members.

15. The system of claim 1, wherein types of member-specific contributed data comprise at least two of omic data, phenotype data, health data, personal data, familial data, demographic data, employment data, and environmental data.

16. The system of claim 15, wherein the determination of the cohorts is initiated based upon analysis of one type of data followed by analysis of different types of data.

17. The system of claim 1, wherein the processing circuitry permits contributing members to opt out of analysis to determine cohorts.

18. The system of claim 1, wherein the processing circuitry permits contributing members or third parties to request that other members contribute additional data to improve a statistical fit of data from potential cohort members of a determined cohort group.

19. The system of claim 1, wherein the processing circuitry permits contributing members or third parties to request that other members contribute additional data to improve a statistical fit of data from potential cohort members of a determined cohort group based on using an analytical tool to identify types of information likely to be valuable in improving the statistical fit.

20. The system of claim 1, wherein the processing circuitry is configured to perform quality control operations on the member-specific contributed data prior to determination of the cohorts.

21. The system of claim 1, wherein the processing circuitry transfers an asset amount to each member-specific account based upon the member-specific value, and wherein the member-specific value is attributed as a currency and/or a cryptocurrency and/or an ownership share in the database or database maintaining company.

22. The system of claim 1, wherein the processing circuitry is configured to make ledger entries in an immutable and/or cryptographically encoded ledger and/or a blockchain based upon interaction with the contributing members.

23. A system comprising:
- a server device including a processor and memory that cooperate to, in operation, facilitate interaction with contributing members of an aggregation;
- a database maintained by an administrative entity that, in operation, stores and aggregates member-specific contributed data transmitted by contributing members with member-specific contributed data contributed by other contributing members; and
- processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;
- wherein the stored and aggregated member-specific contributed data is de-identified from the member-specific account data; and
- wherein at least part of the member-specific contributed data is transformed from a form received from contributing members to a structured and standard format prior to storage in the database and the aggregation is performed on the structured and standard format member-specific contributed data; and
- wherein the processing circuitry analyzes the aggregated member-specific contributed data to determine cohorts of contributing members based upon correlations between the member-specific contributed data for each contributing member, wherein a cohort is determined based upon a criterion established by a third party analysis of the aggregated member-specific contributed data by a third party; and
- wherein the member-specific value is at least partially based upon use of the member-specific contributed data of a respective contributing member by the third party; and wherein the processing circuitry permits communications with contributing members of a cohort without revealing identification of respective contributing members to the administrative entity.

24. The system of claim 23, wherein the processing circuitry determines the cohorts based upon analysis of the aggregated member-specific contributed data initiated by identification of a physical condition potentially detectable from the aggregated member-specific contributed data.

25. The system of claim 24, wherein the processing circuitry determines the cohorts based upon a patient health journey detectable from the member-specific contributed data of the respective contributing member.

26. A system comprising:
a server device including a processor and memory that cooperate to, in operation, facilitate interaction with contributing members of an aggregation;
a database maintained by an administrative entity that, in operation, stores and aggregates member-specific contributed data transmitted by contributing members with member-specific contributed data contributed by other contributing members; and
processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;
wherein the stored and aggregated member-specific contributed data is de-identified from the member-specific account data; and
wherein at least part of the member-specific contributed data is transformed from a form received from contributing members to a structured and standard format prior to storage in the database and the aggregation is performed on the structured and standard format member-specific contributed data; and
wherein the processing circuitry permits periodic analysis of the aggregated member-specific contributed data by both an administrative entity and a third party to determine cohorts of contributing members based upon correlations between the member-specific contributed data for each contributing member; and
wherein the processing circuitry permits communications with contributing members of a cohort by the administrative entity, other members of the cohort, and third parties, without revealing identification of respective contributing members to the administrative entity.

27. The system of claim 26, wherein a cohort is determined based upon at least one parameter that is common to all contributing members of the determined cohort.

28. The system of claim 26, wherein a cohort is determined based upon a criterion established by third party analysis of the aggregated member-specific contributed data.

29. The system of claim 26, wherein the processing circuitry determines the cohorts by episodic analysis of the aggregated member-specific contributed data, or upon contribution of data by a new member, or upon entry of new contributed data by an existing member, or following correcting, updating, or improving a statistical fit.

30. A system comprising:
a server device including a processor and memory that cooperate to, in operation, facilitate interaction with contributing members of an aggregation;
a database maintained by an administrative entity that, in operation, stores and aggregates the member-specific contributed data transmitted by contributing members with member-specific contributed data contributed by other contributing members; and
processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;
wherein the stored and aggregated member-specific contributed data is de-identified from the stored member-specific account data; and
wherein at least part of the member-specific contributed data is transformed from a form received from contributing members to a structured and standard format prior to storage in the database and the aggregation is performed on the structured and standard format member-specific contributed data; and
wherein the processing circuitry analyzes the aggregated member-specific contributed data to determine cohorts of contributing members based upon correlations between the member-specific contributed data for each contributing member, wherein a cohort is determined based upon a criterion established by a third party analysis of the member-specific contributed data; and
wherein the processing circuitry permits communications with contributing members of a cohort without revealing identification of respective contributing members to the administrative entity.

31. A system comprising:
a server device including a processor and memory that cooperate to, in operation, facilitate interaction with contributing members of an aggregation;
a database maintained by an administrative entity that, in operation, stores and aggregates the member-specific contributed data transmitted by contributing members with member-specific contributed data contributed by other contributing members; and
processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;
wherein the stored and aggregated member-specific contributed data is de-identified from the stored member-specific account data; and
wherein at least part of the member-specific contributed data is transformed from a form received from contributing members to a structured and standard format prior to storage in the database and the aggregation is performed on the structured and standard format member-specific contributed data; and
wherein the processing circuitry analyzes the aggregated member-specific contributed data to determine cohorts of contributing members by periodic analysis of the member-specific contributed data to determine correlations between the member-specific contributed data for each contributing member; and wherein the member-specific value is at least partially based upon use of the member-specific data of the respective contributing member by a third party; and wherein the processing circuitry permits communications with contributing members of a cohort without revealing identification of respective contributing members to the administrative entity.

32. A system comprising:

a server device including a processor and memory that cooperate to, in operation, facilitate interaction with contributing members of an aggregation;

a database maintained by an administrative entity that, in operation, stores and aggregates the member-specific contributed data transmitted by contributing members with member-specific contributed data contributed by other contributing members; and processing circuitry maintained by the administrative entity that, in operation, processes member-specific account data received from the contributing members via interface pages to establish member-specific accounts based on the member-specific account data, and attributes a member-specific value to the member-specific accounts based upon respective member-specific contributed data;

wherein the stored and aggregated member-specific contributed data is de-identified from the stored member-specific account data; and wherein at least part of the member-specific contributed data is transformed from a form received from contributing members to a structured and standard format prior to storage in the database and the aggregation is performed on the structured and standard format member-specific contributed data; and wherein the processing circuitry permits analysis the aggregated member-specific contributed data by both an administrative entity and a third party to determine cohorts of contributing members based upon correlations between the member-specific contributed data for each contributing member, wherein a cohort is determined based upon a criterion established by a third party analysis of the member-specific contributed data; and wherein the processing circuitry permits communications with contributing members of a cohort by the administrative entity, other members of the cohort, and third parties, without revealing identification of respective contributing members to the administrative entity.

* * * * *